United States Patent [19]
Hogan et al.

[11] Patent Number: 5,794,621
[45] Date of Patent: Aug. 18, 1998

[54] SYSTEM AND METHOD FOR MEDICAL IMAGING UTILIZING A ROBOTIC DEVICE, AND ROBOTIC DEVICE FOR USE IN MEDICAL IMAGING

[75] Inventors: Neville Hogan, Sudbury; Hermano Igo Krebs, Somerville, both of Mass.

[73] Assignee: Massachusetts Institute of Technology, Cambridge, Mass.

[21] Appl. No.: 553,021

[22] Filed: Nov. 3, 1995

[51] Int. Cl.[6] ...................................................... A61B 5/05
[52] U.S. Cl. ........................... 128/653.1; 128/653.2; 128/774
[58] Field of Search ..................... 128/653.1, 653.2, 128/774; 606/130; 901/30, 14-18, 6; 272/93

[56] References Cited

U.S. PATENT DOCUMENTS

| | | |
|---|---|---|
| 3,648,143 | 3/1972 | Harper et al. |
| 4,235,437 | 11/1980 | Ruis et al. ................. 272/134 |
| 4,791,934 | 12/1988 | Brunnett |
| 4,936,299 | 6/1990 | Erlandson |
| 5,018,724 | 5/1991 | Maser et al. |
| 5,042,462 | 8/1991 | Bremer |
| 5,078,140 | 1/1992 | Kwon |
| 5,184,319 | 2/1993 | Kramer |
| 5,205,289 | 4/1993 | Hardy et al. |
| 5,230,338 | 7/1993 | Allen et al. |
| 5,251,127 | 10/1993 | Raab |
| 5,305,203 | 4/1994 | Raab |
| 5,308,352 | 5/1994 | Koutrouvelis |
| 5,339,812 | 8/1994 | Hardy et al. |
| 5,339,813 | 8/1994 | Deyoe et al. |
| 5,354,314 | 10/1994 | Hardy et al. |
| 5,397,323 | 3/1995 | Taylor et al. |
| 5,408,409 | 4/1995 | Glassman et al. |
| 5,427,097 | 6/1995 | Depp |

FOREIGN PATENT DOCUMENTS

| | | |
|---|---|---|
| 0371156 | 6/1990 | European Pat. Off. |
| 4-303424 | 10/1992 | Japan |
| 2239523 | 7/1991 | United Kingdom |

*Primary Examiner*—Marvin M. Lateef
*Assistant Examiner*—Eleni Mantis Mercader
*Attorney, Agent, or Firm*—Oblon, Spivak, McClelland, Maier & Neustadt, P.C.

[57] ABSTRACT

A robotic device for use in conjunction with an imaging system and an imaging method is provided. The robotic device can provide mechanical measurements within the imaging system, and can also control the mechanical environment within the imaging system. An end effector of the robotic device engages a body segment of the patient. In addition, position and force sensors are associated with the robotic device such that the position and forces applied to the end effector can be sensed/measured and recorded, while images are obtained. In addition, the robotic device includes actuators to move the end effector to a desired position, and/or to provide a force to a body segment of a patient by way of the end effector. In a particularly preferred form, structural, sensory, and actuator components of the robotic device are magneto-translucent, such that the robotic device can control and/or provide measured information regarding the mechanical environment within a magnetic resonance imaging system.

49 Claims, 13 Drawing Sheets

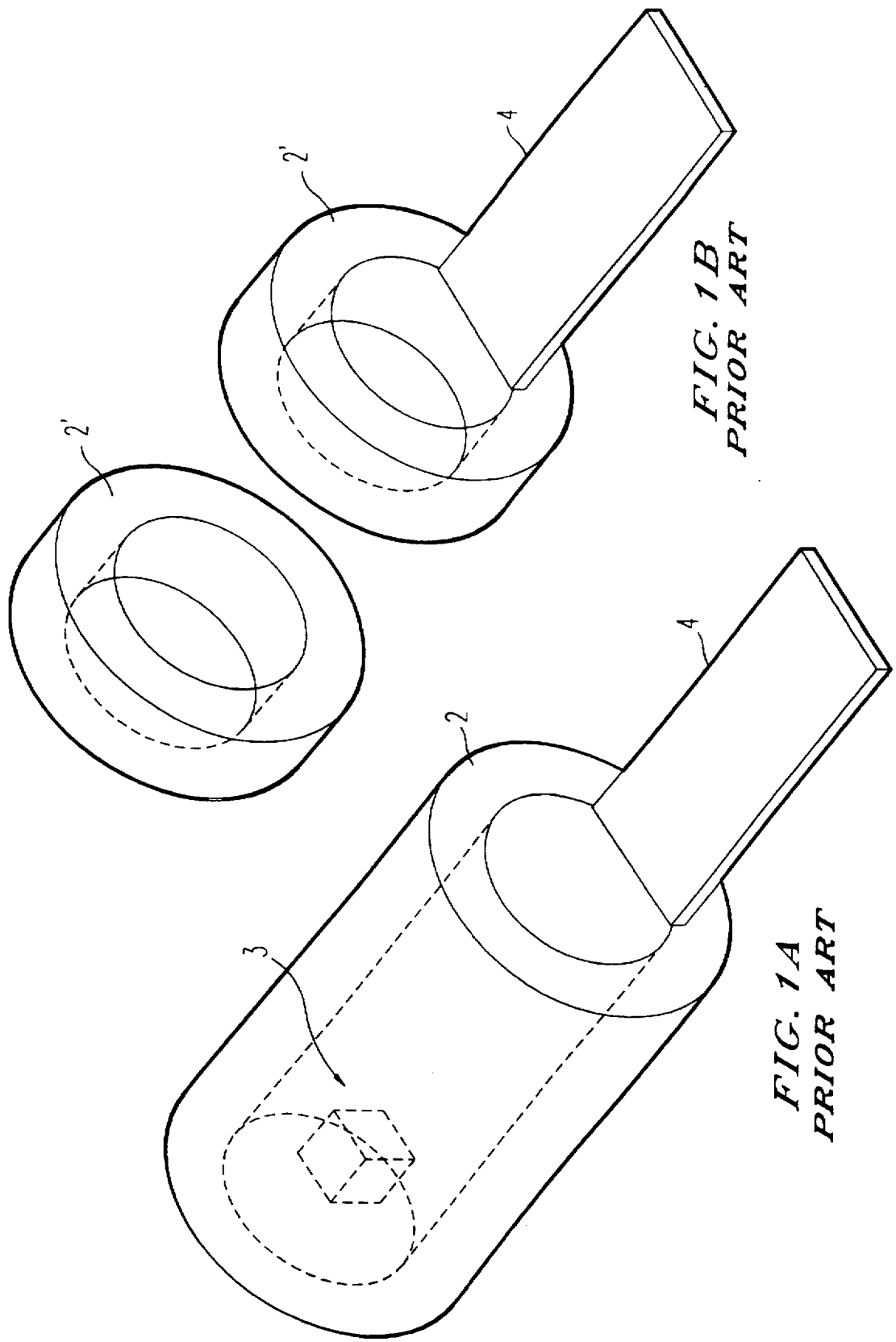

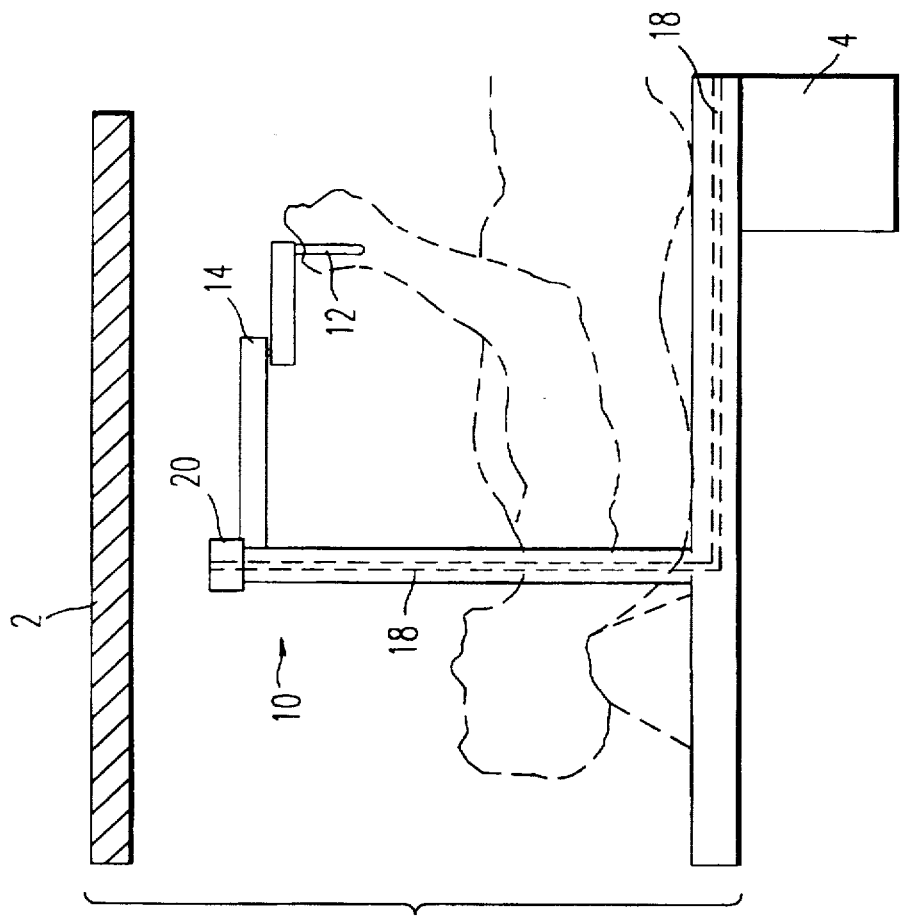
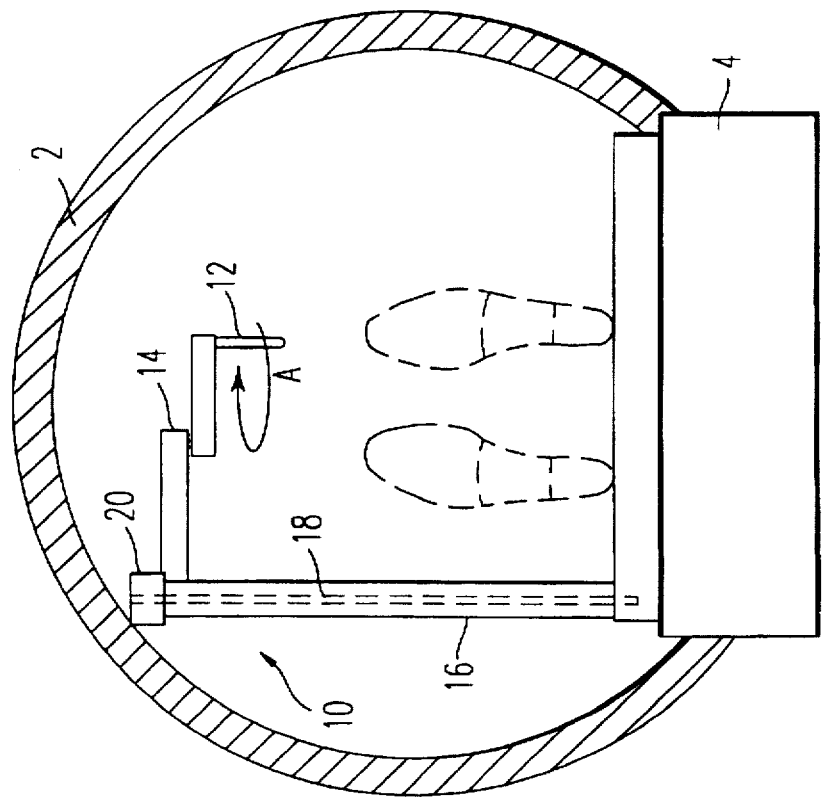

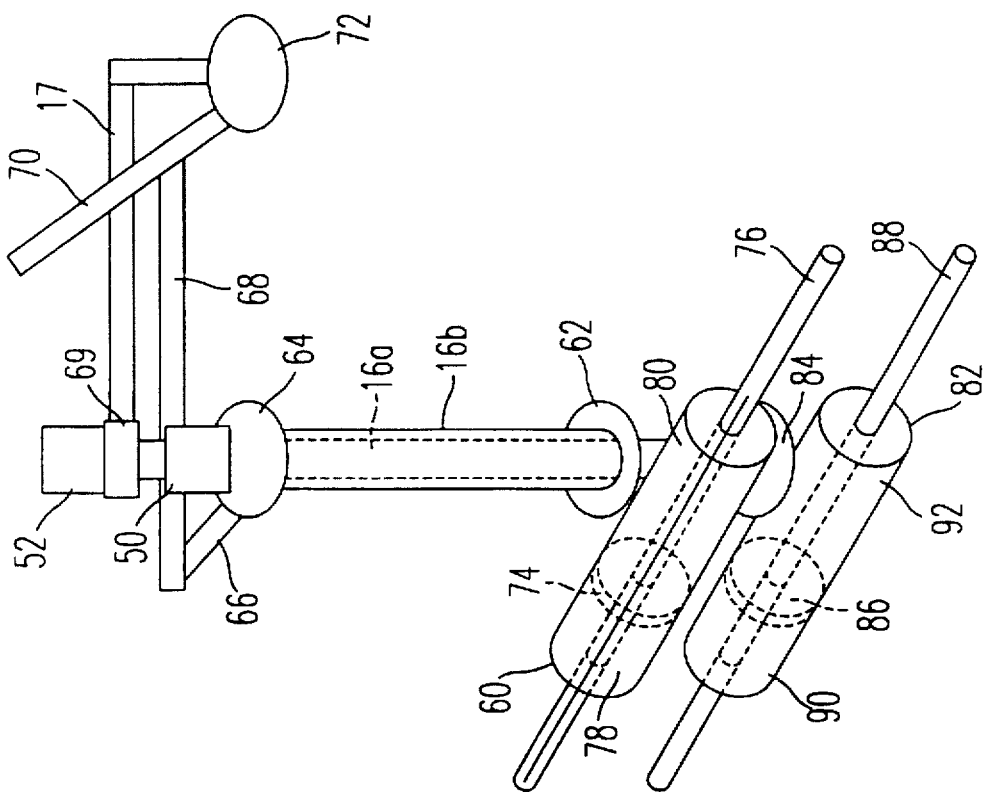
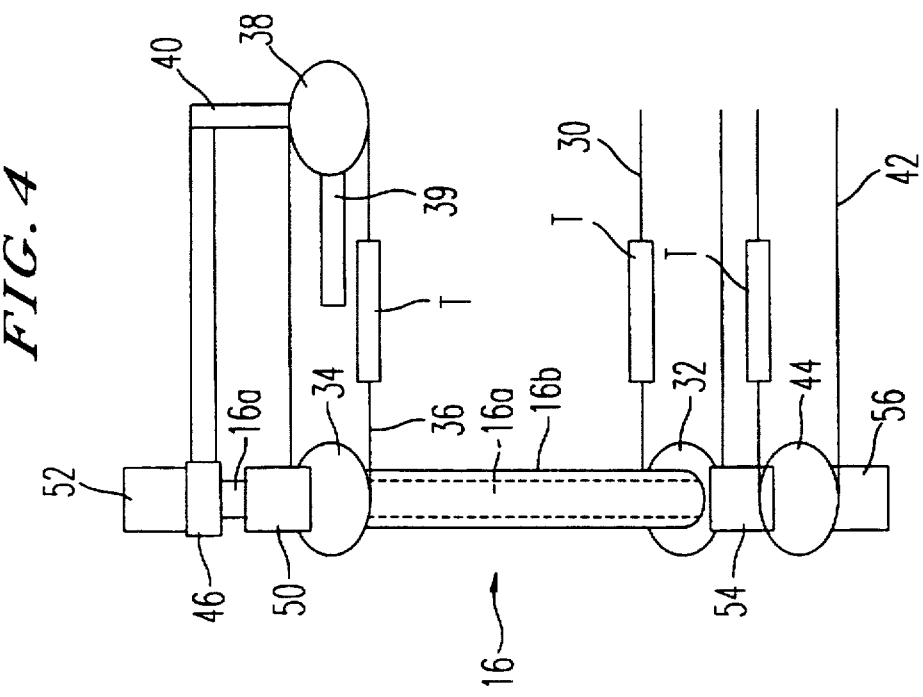

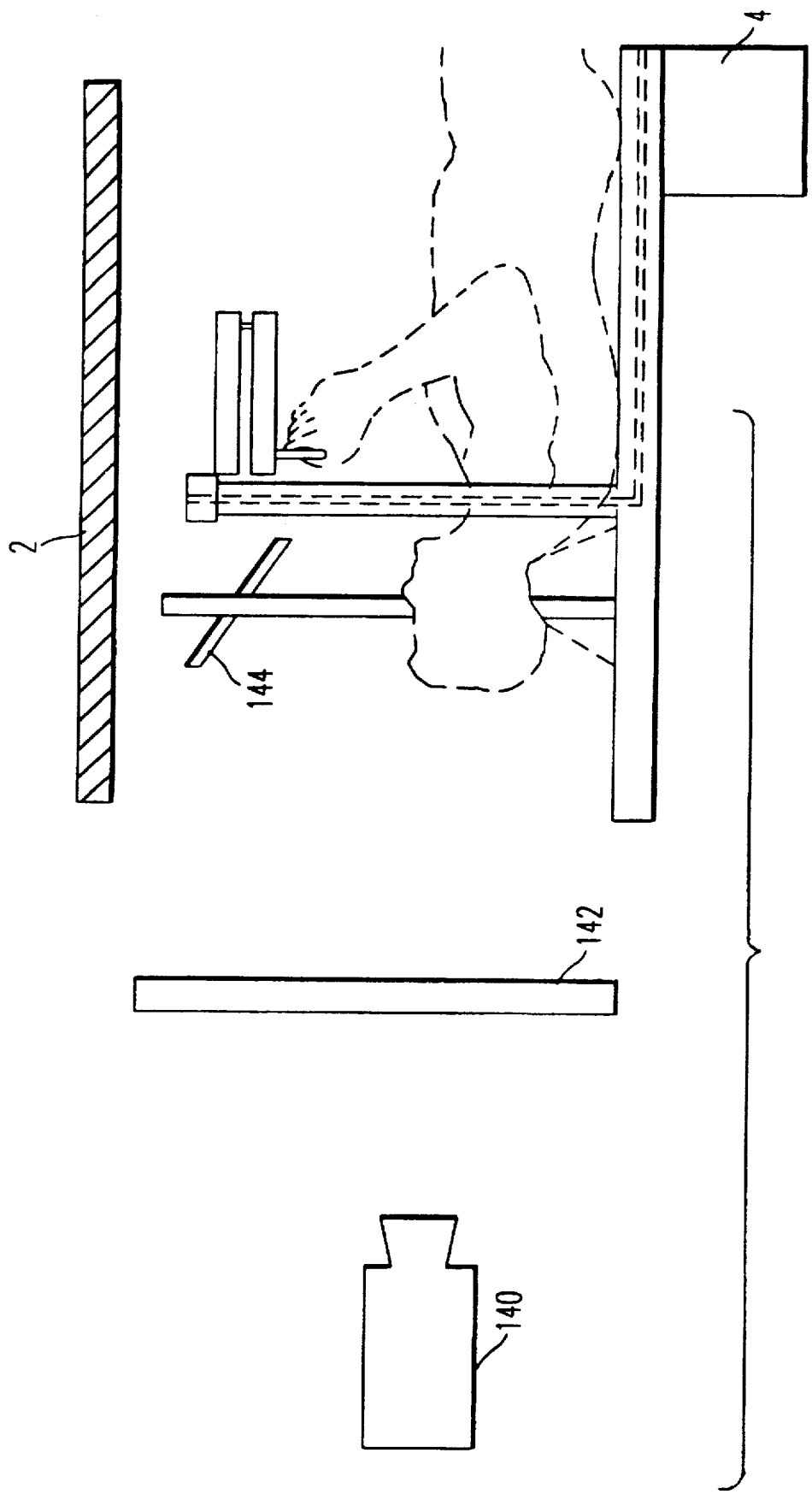

SYSTEM AND METHOD FOR MEDICAL IMAGING UTILIZING A ROBOTIC DEVICE, AND ROBOTIC DEVICE FOR USE IN MEDICAL IMAGING

BACKGROUND OF THE INVENTION

1. Field of the Invention

The invention relates to a system and method for medical imaging utilizing a robotic device, and a robotic device for use in medical imaging. The invention can be advantageously utilized, for example, in providing images for diagnostic and/or therapeutic purposes, or in assessing pharmaceutical intervention, with the robotic system providing mechanical measurements, and/or controlling the mechanical environment within the imaging system.

2. Discussion of the Background

Medical imaging systems are well-known for use in diagnosing various medical disorders. Examples of such imaging systems are computerized tomography (CT), positron emission tomography (PET) and magnetic resonance imaging (MRI or NMR). Typically such systems are utilized to diagnosis disorders by obtaining images while the patient is stationary and disposed within the imaging system (or within a field of the imaging system).

In addition to imaging a stationary patient/subject, imaging systems have also been utilized for imaging a patient performing a simple repetitive motion. For example, U.S. Pat. No. 4,441,502 to Chance discloses an NMR system which determines a relationship between work output and the oxidation phosphorylation capability in an exercising body member. Chance provides a crank member within an imaging system, with the crank linked to an ergometer disposed outside of the imaging system (i.e., outside of the imaging coil or field). While a patient turns the crank member, the NMR system is utilized to determine the relationship between the work rate of the patient and the mitochondrial metabolic state of the patient's muscle tissue. However, the Chance arrangement is limited to a hand lever or crank-type arrangement, which allows the user/patient to perform only a single task, and the system of Chance is limited to obtaining metabolic activity as a function of exertion or work. Chance does not allow for the performed task to be varied, and does not allow for the correlation of images with varying mechanical conditions during imaging. In addition, while the crank of Chance can receive work or motion from a patient, it cannot impart motion or a force to a patient, and is not continuously reprogrammable by a computer.

SUMMARY OF THE INVENTION

It is an object of the present invention to provide a robotic device for use in an imaging system and method.

It is another object of the invention to provide a robotic device which provides spatial position information regarding a body segment of a patient during imaging of the patient.

It is yet another object of the invention to provide a robotic device which includes actuators and/or position sensors suitable for use within an image system.

It is a further object of the invention to provide a robotic device which includes an end effector which is coupled to or engages a body segment of a patient disposed within an imaging system, such that images of the patient can be obtained while the robotic device provides position and/or force information associated with the end effector or body segment.

It is also an object of the present invention to provide an imaging system and method which can obtain images while a patient or subject is performing one (or more) of a variety of manipulative tasks.

It is another object of the invention to provide an imaging system and method which can obtain images while a patient or subject is learning to perform one (or more) of a variety of manipulative tasks.

It is yet another object of the invention to provide an imaging system and method which can obtain brain images to determine the location and/or amount of brain activity resulting from a patient's learning of a manipulative task, or resulting from a patient's performance of a previously learned manipulative task.

It is still another object of the invention to provide a robotic system which can assist in (1) teaching manipulative tasks to a patient and/or (2) receiving manipulative tasks performed by a patient, while sensing or measuring one or more quantities associated with the manipulative tasks, and with images of the patient obtained during learning or performance of a task.

It is a further object of the invention to provide a robotic system for use in magnetic resonance imaging, with the robotic system including magneto-translucent sensing components and magneto-translucent structural components disposed inside of the imaging system which do not adversely affect and are not adversely affected by the imaging system, and with the robotic system further including sensing or measuring components (e.g., light sources and transducers) disposed outside of the imaging system which are coupled to the components disposed inside of the imaging system.

It is a still further object of the invention to provide an imaging system and method which includes a robotic device disposed inside of an imaging system, with the robotic device including one or more actuators which can (1) assist a patient in learning a manipulative task, and/or (2) provide an opposition force as part of a manipulative task being performed by a patient, (3) provide any desired force to a body segment of, and/or (4) move an end effector of the robotic system to various locations within an imaging system to engage a body segment of a patient.

It is another object of the invention to provide a robotic imaging system and method which can both measure (1) motor movement while a patient is learning or performing a task, and (2) neural or brain activity associated with the task.

It is yet another object of the invention to provide an imaging system and method which includes a robotic device coupled to or engaging a body segment of a patient, so that the robotic device provides sensed information regarding the body segment and/or imparts forces to the body segment while images are taken of the same or a different body segment.

The above as well as other objects and advantages are achieved in accordance with the present invention which provides a diagnostic/therapeutic imaging system and method utilizing a robotic device, and a robotic device therefor. The robotic device includes an end effector which is coupled to or engages a body segment of a patient, with the robotic device providing sensed information (position and/or force information), while the imaging system provides image information which can be correlated with the activity of the body segment (or the end effector). The robotic device further includes actuators for moving the end effector and/or applying forces with the end effector. In addition, the robotic device is programmable to allow various and changeable tasks to be performed by the robotic device within an imaging system. Thus, the robotic device can control and/or provide measured information regarding the mechanical environment within an imaging system while images are obtained. The imaging system can obtain images of the same body segment engaged by the end effector. However, images can also be obtained of a body segment other than that engaged by the robot/end effector, to thereby provide information regarding the relationship between the body segments. As a result, the understanding of various biological systems can be enhanced, thereby allowing various disorders to be identified or better understood, and also allowing analysis of any treatment/therapy (e.g. to determine the efficacy or optimal use of a therapeutic or pharmacologic approach).

By way of example, in accordance with one application of the invention, images are obtained while a patient is performing or learning manipulative tasks associated with movement of a handle member (with the handle serving as the "end effector"), which movement is measured and/or controlled by the robotic system. With this system/method, magnetic resonance imaging is utilized to determine the location and/or quantity of brain activity while a patient is performing or learning one of a variety of manipulative tasks. By utilizing magnetic resonance imaging to obtain brain images while a patient is performing or learning a manipulative task, the amount of brain activity can be measured and correlated with the task as sensed and recorded by the robotic system. As a result, knowledge regarding brain or neural functions in relation to motor functions can be enhanced. For example, in applying the present invention to obtain brain images associated with manipulative tasks (with a handle coupled to the patient), it has been verified that different locations of the brain are utilized for learning a task as compared with performing a previously learned task.

The imaging and robotic system/method of the present invention can provide useful diagnostic information, which can assist in identifying or better understanding a disorder. Moreover, the system can be utilized for therapeutic purposes, since the response to a particular medication or a particular dosage of a medication can be identified, thereby assisting in determining the efficacy of a medication or optimizing its use.

The robotic system provides measured mechanical information by position and force sensors associated with a robot. In addition, the robot preferably includes one or more actuators for movement of an end effector which engages a body segment of a patient, and for the application of forces to the body segment by way of the end effector. The robotic device is also programmable and continuously reprogrammable, allowing the robotic device to provide a variable control over the mechanical environment within an imaging system. Thus, the robotic system can provide measured mechanical information while the body segment is moving and/or applying a force to the end effector, and also while the end effector is moving and/or applying a force to the body segment. The mechanical information can then be correlated with image information obtained by the imaging system.

An example of a robotic system of the present invention includes a handle member as an end effector, which can be grasped by the patient's hand (or other extremity), or the patient can be attached to the handle, e.g., by a custom made hand holder. The patient can learn a manipulative task utilizing actuators which move the robot (and thus the patient's hand or other body segment) through one or more tasks, with the actuators producing movement of the robotic system according to a selected one of a plurality of preprogrammed sequences. Alternately, the patient can learn a manipulative task by viewing a visual image or visual instructions, and manipulating the robot according to the instructions provided by the visual image/instructions. Once a patient has learned a particular task, the patient can then perform the task as instructed by an attendant or a visual display. As a result, images can be obtained while the patient is learning or performing a task or tasks, and the images can be correlated with the tasks. In addition, the patient can perform a previously learned task, and a perturbation or unexpected resistance force can be supplied by the robotic system, such that an image can be obtained while the patient is performing a previously learned task which is interrupted by an unexpected (i.e., unexpected to the patient) perturbation.

It is to be understood that the present invention is not limited to the use of a handle member as an end effector, or to imaging while performing manipulative tasks. In particular, other forms of end effectors can be utilized in conjunction with the magneto-translucent robotic device of the present invention can include other types for controlling and measuring mechanical conditions within an imaging system. In addition, various aspects of the magneto-translucent robotic device of the present invention may be advantageously utilized within various magnetic fields (in addition to imaging systems), such as in magnetic field environments associated with magnetic levitation, particle accelerators, magnetic confinement fusion devices, cryogenic superconductor generators, power line maintenance, etc.

Although certain aspects of the present invention may be utilized with different imaging techniques, MRI is presently preferred. In particular, some imaging techniques, such as PET imaging, are disadvantageous in that the patient is exposed to radioactivity, and thus the number of imaging sessions for a particular patient must be limited. In addition, PET machines and associated accelerator devices (typically a cyclotron) are more expensive as compared with an MRI machine. Further, the resolution of a PET machine is lower than that of an MRI machine. Utilizing MRI, images of a particular patient can be obtained much more frequently as compared with imaging techniques which subject the patient to radioactivity. Therefore, images can be repeatedly obtained during a diagnostic/therapeutic session, and more frequent diagnostic/therapeutic sessions are possible.

To correlate the images with the mechanical environment within the imaging system, sensors are associated with the robotic device to indicate one or more of the position, velocity, and/or forces associated with various tasks. In order to avoid interference of the robotic system (and sensors associated therewith) with the imaging system, components of the robotic system which are disposed inside of the MRI are magneto-translucent. By way of example, the structural components of the robot can be formed of aluminum, copper, gold, silver, wood, or most organic materials which do not include iron (polytetrafluoroethylene, nylon, carbon graphite, ceramics, etc.). The sensor components can utilize a light source based sensor, with the light source disposed outside of the imaging system, and with the light conveyed into the system utilizing an optical fiber or optical cable. One or more magneto-translucent sensors are disposed inside of the MRI to provide position, velocity, and/or force information, with the resulting sensed information conveyed outside of the MRI utilizing another optical fiber or cable. The body or motor movement associated with robotic tasks can thus be correlated with images obtained during the tasks.

The robotic system also includes actuators to guide the patient through a task. or to provide one or more resistance forces while a patient is performing a task. The actuators can also move the end effector to a particular body segment. or apply a desired force/pressure to a body segment. Portions of the actuators which are disposed inside of the imaging system are magneto-translucent. Cables and hydraulic actuators are disclosed herein. however it is also possible to utilize other types of actuators for practicing the present invention.

The present invention thus integrates robotic technology with imaging technology. particularly functional magnetic resonance imaging. and provides new techniques for advancing understanding of biological systems. These techniques can be utilized to diagnose disorders and possibly determine the cause of such disorders. In addition. the integration of robotic and imaging technologies can be utilized therapeutically to measure progress associated with a particular treatment. or to provide a faster and better quantified understanding of the effects. delivery and efficacy of drugs.

BRIEF DESCRIPTION OF THE DRAWINGS

A more complete appreciation of the invention and many of the attendant advantages thereof will become readily apparent from the following detailed description. particularly when considered in conjunction with the accompanying drawings in which:

FIGS. 1A and 1B schematically depict magnetic resonance imaging systems;

FIGS. 2A and 2B are end and side views of a robotic imaging system of the present invention. including a rotational robotic embodiment;

FIG. 4 depicts sensors and cable actuators for the rotational robot embodiment of the present invention;

FIG. 5 is a modified form of the FIG. 4 embodiment. in which cables are replaced with hydraulic actuators;

FIGS. 8A–8C depict arrangements for providing a visual display to a patient disposed within the imaging system;

DESCRIPTION OF THE PREFERRED EMBODIMENTS

Figure 2C:
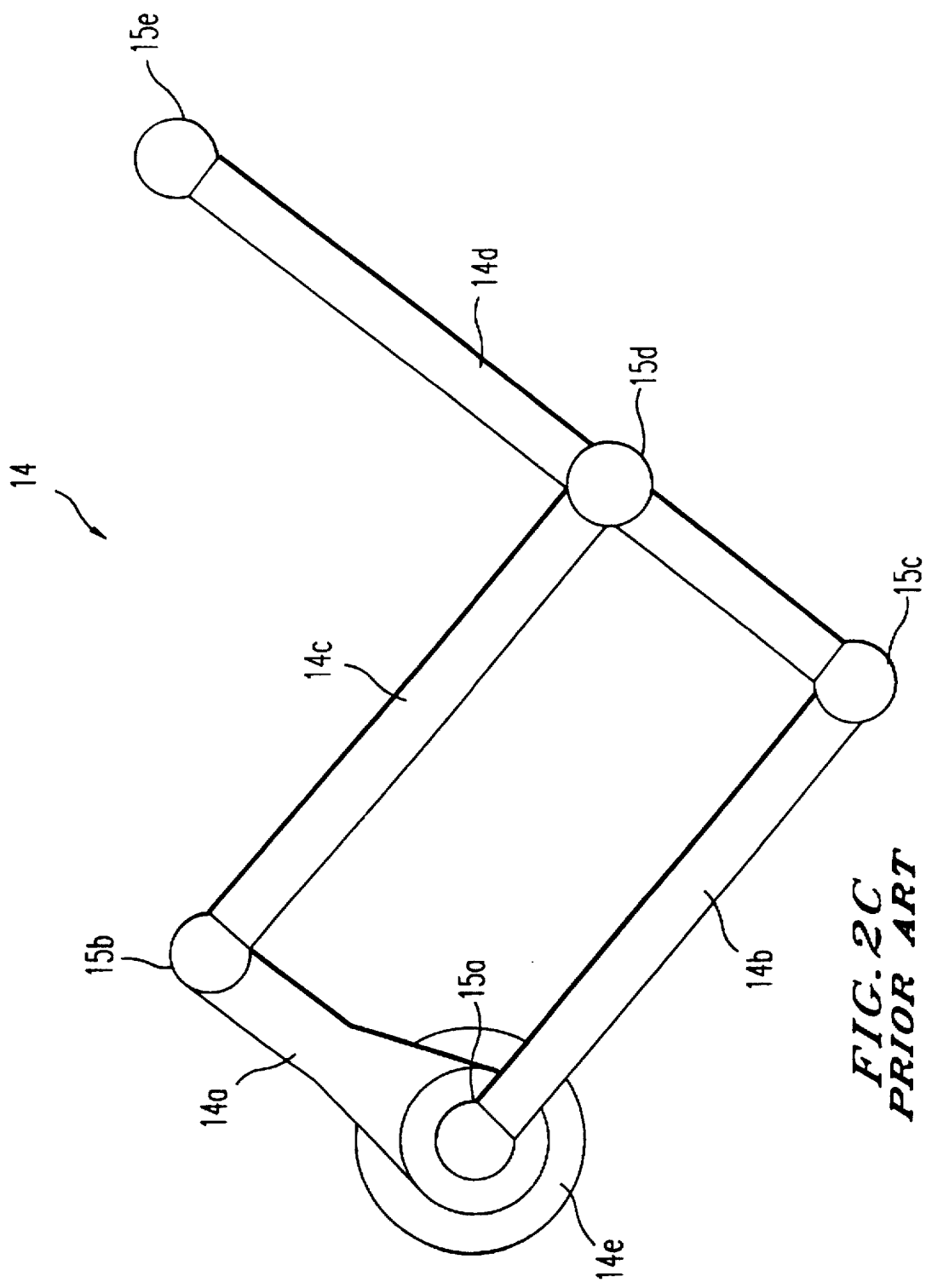
FIG. 2C is a top or plan view of a five-bar linkage which can be utilized in the rotational embodiment of FIGS. 2A and 2B.

In accordance with the present invention. a robotic device is provided which is capable of functioning within a strong magnetic field. without being adversely affected by the magnetic field. The robotic device is preferably computer programmable. and is capable of sensing and/or generating forces or motion or both. In a presently preferred form. an end effector and mounting assembly are formed of magneto-translucent materials. In addition. magneto-translucent position and force sensors are disclosed herein. as are magneto-translucent actuator arrangements. which provide a robotic device which can fully function within severe magnetic fields as encountered. for example. in an MRI system.

In accordance with a presently preferred form of the invention. the robotic system is provided for controlling and/or providing measured information with regard to the mechanical environment within an imaging system. The robotic system includes an end effector which is coupled to or engages a body segment of a patient. In accordance with one example of the invention. a handle member is grasped by the patient such that the handle member moves in concert with movement of the patient's hand. However. since the robotic system can be coupled to or engage other body segments. the term "end effector" is utilized herein to refer to the component of the robotic system which engages a body segment. Of course. the end effector may also be adapted to engage an object other than a body segment if desired (e.g.. if the robotic device is utilized in a magnetic field other than in an imaging system). The robotic system includes position or location sensors to provide position information regarding the end effector and thus the body segment. In addition. force or torque sensors are provided for measuring the force between the end effector and the body segment (either applied by the body segment to the end effector. or applied by the end effector to the body segment). In addition. actuators are provided to control movement of the robotic system and/or for the application of force to the body segment by the end effector. In addition to providing measured mechanical information. the sensors also provide information utilized for controlling the actuators of the robotic system.

By providing a robotic system which engages a body segment. mechanical measurements regarding the body segment can be obtained within an imaging system while images are obtained by the imaging system (which can be of the same body segment to which the end effector is coupled. or of a different body segment). In addition. the actuators associated with the robotic system allow the robotic system to control the mechanical environment within the imaging system. The robotic system is also programmable and continuously reprogrammable such that tasks performed within the imaging system can be varied.

In selecting materials for the various components of the robotic system. there are two categories which can be considered. First. if the robot is to operate continuously. the robot must be fully compatible with the MRI machine at all times. However. it is also possible to provide for intermittent movement of the robot. in which the robot is not fully compatible with the MRI machine. however the non-compatible component(s) operate only during down time of the MRI (when images are not being obtained or between images). Since images will preferably be obtained relatively frequently (on the order of hundreds of milliseconds. up to one image per second). continuous robot movement (full compatibility) is presently preferred. For full compatibility of the robot with respect to the imaging system. the imaging system and associated magnetic field should not adversely affect the robot or impart forces to the robot. and the robot should not adversely affect images obtained by the MRI. The magnetic field of the MRI exerts a strong attractive force to any ferromagnetic components and can damage any ferromagnetic parts formed of. e.g.. carbon steel or pure nickel (as typically associated with bearings, bolts, etc.). Thus, ferromagnetic materials are not acceptable. Highly paramagnetic materials, such as stainless steel and titanium can encounter slight forces from the magnetic field, and can be utilized if they are properly secured and of sufficient strength. Low paramagnetic materials and diamagnetic materials are acceptable, examples of which are aluminum, water, copper, gold, silver, and most organic materials which do not include iron (e.g., polytetrafluoroethylene, nylon, carbon graphite, ceramics, etc.). In addition, since the MRI produces an audio frequency of 200 Hz to 1 KHz, and since a cryogenic pump is typically operating at 1 Hz, audio sensitive equipment should be avoided. Conductors which move with the robot should be particularly avoided, since an electric current can be generated as a conductor moves within a magnetic field. In addition, electrical eddy currents should be avoided to prevent distortion of the magnetic field and also to prevent safety hazards. By way of example, the robot can be formed of a composite material or wood. For a cable driven actuator arrangement, nylon or plastic cables or pulleys can be utilized. Similarly, with the hydraulic-driven actuator system, plastic cylinders (acrylic, polycarbonate, etc.) can be utilized, with oil as the hydraulic fluid (of course, other fluids are also possible). For the position and force sensors, ceramic or teflon bearings can be utilized to support the sensors, with the sensors formed of, e.g., plastics or glass.

Referring now to the drawings wherein like reference numerals designate identical or corresponding parts throughout the several views, FIGS. 1A and 1B schematically depict known MRI machines. FIG. 1A depicts a standard MRI machine which includes a cylindrical coil housing 2, and a movable table 4 which moves the patient into and out of the coil housing 2. FIG. 1B is an alternate example, referred to as an "open" MRI machine, in which spaced coil housings 2' are provided, and the movable table 4 inserts the patient between the coils. The open MRI can be advantageous for large or claustrophobic patients. However, the standard MRI will typically produce better images, since it provides a stronger magnetic field (e.g., 1.5 T for the standard MRI as compared with 0.5 T for the open MRI). Other MRI configurations are also known, and can be utilized in accordance with the present invention.

In accordance with one application of the present invention, functional magnetic resonance imaging is utilized, which can measure, e.g., the local level of oxygenation of the blood. To provide functional MRI, a main coil is disposed in the coil housing(s) 2, 2' to provide a magnetic field. In addition, an echoplanar coil is also housed within the coil housing(s) and is utilized to generate a field gradient so that different "slices" of the patient can be imaged. Further, an rf coil is associated with and disposed within a cage member (schematically represented at 3 in FIG. 1A) which is placed about a portion of the patient at which an image is desired (e.g., about the patient's head to image the brain in one form of the present invention). The rf coil, disposed about a portion of the patient, is used as a sensor or measuring device for obtaining images. MRI systems and functional MRI are known, and therefore, further details are not provided herein.

Further, in accordance with an exemplary application of the present invention, functional MRI is utilized to determine/measure brain activity by measuring the blood oxygenation level. (Other indicia can be measured if a different imaging method is to be utilized, e.g., utilizing PET, the regional concentration of blood flow or glucose consumption can be measured.) Initially, an image (or plural images for different slice locations) is taken while the patient is stationary to provide a baseline condition or reading. Next, one or more images are taken while the patient is learning or performing a task, to obtain measurements (e.g., of blood oxygenation) associated with the task or activity. The images (and measurements therefrom) can be taken at various slice locations, and at various time intervals while the patient is learning/performing a task. The baseline measurement for a corresponding slice is then subtracted from each task associated measurement, with the resulting difference corresponding to the increase in activity or increase in brain function associated with the task for each area or region of the brain. Thus, brain function or activity associated with a particular task is measured by measuring a corresponding change in blood oxygenation.

By obtaining images of, e.g., the brain, while the patient is performing a particular task, cellular brain activity can be correlated with measured quantities associated with the task as measured utilizing the magneto-translucent robotic system. The quantities measured utilizing the robotic system can include one or more of position, velocity and force associated with movement of the patient's limb while learning or performing a task. Thus, utilizing functional brain imaging, the MRI provides images from which the amount of neural computations or "inputs" to the neuro-motor system can be derived, while the magneto-translucent robotic system controls the mechanical environment, including the sensory-motor stimuli and neuro-motor functional responses or "outputs." Typically, MRI scanners operate in a range of 60–70 MHz (Lamar frequency range). Therefore, electromagnetic interference by the robotic system in that range should be avoided.

Of course, the present invention is not limited to brain imaging, since images of other body segments may also be obtained while the robotic system measures and controls the mechanical environment. For example, images may be taken of the spine or other organs or body segments, while the robotic system is controlling and providing measured information regarding the mechanical environment of the same or a different body segment as that being imaged. Further, the present invention is not limited to a handle type end effector, or to the learning or performance of manipulative tasks during imaging. For example, the robotic system could also be utilized to apply static or dynamic forces to a body segment while images are obtained, or to palpate a body segment while images are obtained.

For high quality images, an MRI image can be obtained over a relatively long period of time (e.g., eight minutes). However, in accordance with a presently preferred mode of the invention, it is believed that quantitative measurements associated with brain activity will typically be of greater interest (since the brain structure of the patient or subject is known from previous imaging), and therefore images will be obtained in a relatively short period of time (e.g., on the order of hundreds of milliseconds, up to one image per second), so that plural images can be obtained during a particular task.

The robotic system includes an end effector for coupling a body segment of the patient to the robotic system. In addition, the robotic system provides a mounting assembly for movably mounting the end effector so that the end effector can be moved in a plurality of directions, and so that various tasks (or patterns of movement) can be selectively performed while the body segment is coupled to the end effector. The robotic system further includes an actuator system to move the end effector to a desired location to allow the end effector to be coupled to a body segment, or to move the end effector and body segment once the end effector is coupled to the body segment. The actuators also allow the end effector to apply a force or pressure to the body segment (which can be, e.g., a static or dynamic force, palpation, or a force applied during movement of the body segment). The actuators can also be utilized to guide the patient through a task to assist learning of a task, or to perturb performance while a patient is attempting to perform a task.

A sensing system is also associated with the robotic system to provide one or more of position, velocity and force measurements to provide mechanical information of the end effector and body segment during imaging, so that either end effector or task performance measurements can be correlated with images (or information obtained from the images). A controller (e.g., a personal computer) is also preferably provided for the robotic system for storing plural preprogrammed (or reprogrammable) sequences to control the actuator system according to a selected sequence. In addition, the controller for the robotic system can store (and output to a display) visual images or visual instructions for a patient to perform a particular task. The task instructions to the patient can include instructions to manipulate a handle member (with the handle serving as an end effector) to a position or according to a particular sequence. However, the instructions may also relate to a variety of other tasks to be performed during imaging while the end effector is coupled to a body segment, e.g. to cough, breathe deeply, etc. The robotic system controller can also receive and store/record measurements taken by the sensing system.

A first embodiment of the robotic imaging system of the present invention is represented in FIGS. 2A and 2B. This embodiment utilizes a rotational configuration to provide the freedom of movement of the end effector. The rotational configuration 10 can be mounted for movement with the movable table 4, or a separate mounting structure can be provided. The depicted rotational configuration includes an end effector 12 in the form of a handle which is connected to a linkage assembly 14. The linkage can be, for example, a standard SCARA five-bar linkage (discussed in further detail hereinafter), however, other linkage or robotic arm configurations are also possible. When provided in the form of a handle, the end effector 12 preferably pivots about its own axis (as indicated by arrow A) with respect to the five-bar linkage 14, such that torsional forces are not generated in the handle itself, and the user can freely move the handle in any desired direction (i.e., in two degrees of freedom in the present embodiment) Although the end effector 12 is shown in the form of a handle which is grasped by a patient, the end effector can take a variety of forms suitable for engaging a body segment of a patient. For example, the end effector can be a custom made hand holder or could be adhesively secured to a body segment. In addition, if desired, the end effector can be a pad or probe which exerts a force or palpates a body segment of a patient.

The five-bar linkage 14 is connected to a support post or shaft assembly 16. Preferably, the support post 16 is hollow, such that optical fibers 18 can be disposed therein for conveying light to sensor components disposed inside of the MRI coil, and for conveying light information (or measurements associated with movement of the end effector) to a location outside of the MRI coil 2. As discussed hereinafter, the support post 16 can include internal and external shafts for coupling the linkage 14 to various types of actuators. One or more sensors represented at 20 are provided to sense/measure information associated with movement of the robot, with the sensor(s) 20 coupled to input and output optical fibers 18.

FIG. 2C is a top view of a SCARA five-bar linkage which can be utilized in the rotational embodiment of the present invention, and which itself is known. The SCARA five-bar linkage includes four bars 14a–14d, with the fifth bar extending vertically (in a direction perpendicular to the drawing figure) or providing a structural continuity between the bars 14a and 14b. The bars are pivotable about respective pivots 15a–15d. The end effector 12 (which extends in a direction perpendicular to the figure with respect to FIG. 2C) is pivotable about its own axis at 15e in the case of a handle type end effector as shown in FIGS. 2A and 2B. Pivoting of the arm 14b about a shoulder pivot 15a determines the location of an elbow pivot 15c, while the additional pivotal movement of arm 14a results in pivotal movement about the elbow for a given position of arm 14b. With this arrangement, position, velocity and force or torque measurements associated with movement of the end effector at 15e can be determined with information associated with the movement of bars 14a and 14b, with the summation of positioning, velocity and/or force information associated with bars 14a and 14b resulting in information associated with movement of the end effector at 15e. Although a five-bar linkage is utilized in the rotational embodiment described herein, it is to be understood that a variety of linkage arrangements are possible for responding to force/movement of the end effector 12 by the patient, and for imparting movement/forces to the patient through the end effector 12. It is also to be understood that, while the present invention provides a robotic system for two degrees of freedom, simpler or more complex robotic systems could be implemented if desired. For example, a simple linear movement robotic system could be utilized, or a more complex robotic assembly could be provided for multiple degrees of freedom.

Figure 3B:
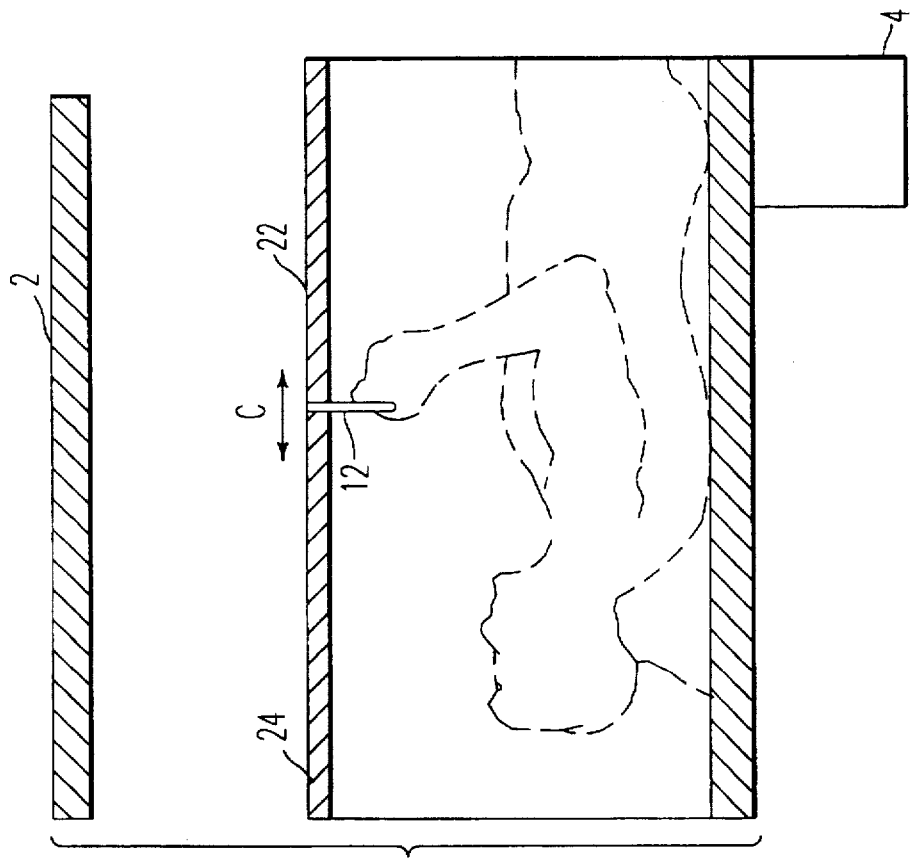
FIGS. 3A and 3B are end and side views of a robotic imaging system including a Cartesian robotic embodiment of the present invention.
Figure 3A:
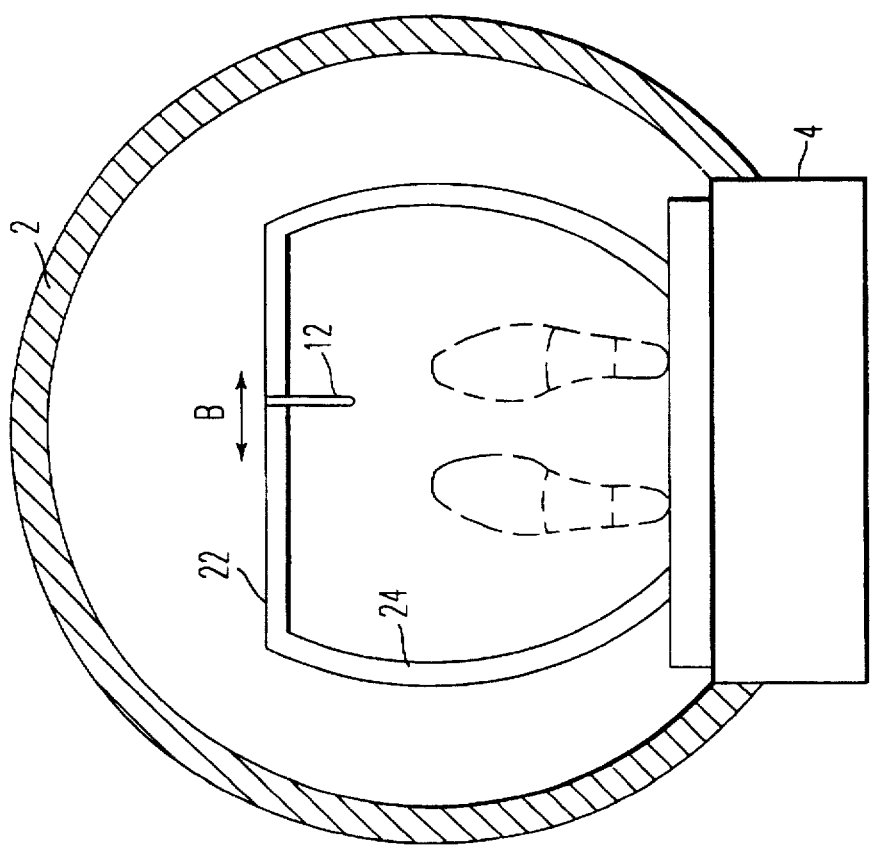

FIGS. 3A and 3B schematically depict an alternative to the rotational embodiment of FIGS. 2A–2C. In this embodiment, a Cartesian configuration is provided in which the end effector 12 is moveable in a transverse direction (represented by arrow B in FIG. 3A) along a transverse support 22. In addition, the transverse support 22 is moveable in a longitudinal direction (represented by arrow C in FIG. 3B) along the support frame 24. Thus, the handle 12 can move in both longitudinal (as the transfer support 22 moves along frame 24) and transverse (as the handle moves along transverse support 22) directions for x–y positioning. As shown in FIG. 3A, the support frame 24 can have a rounded or arcuate configuration to be readily accommodated within the MRI coil 2, while also accommodating a patient within the support frame 24. As with the rotational configuration, sensors or measurement devices are associated with the Cartesian configuration, and optical fibers can extend within or along the frame to carry light from a light source located outside of the MRI coil 2 to a sensor component disposed inside of the MRI coil 2, with optical fibers also conducting or transmitting measurement information from the internal sensor components to a location outside of the MRI coil, as discussed further hereinafter.

FIG. 4 illustrates actuator and sensor/measurement systems which can be utilized with the rotational robotic embodiment. As shown in FIG. 4, the support post 16 can include an internal shaft 16a disposed within an external shaft 16b, with each of the shafts 16a and 16b independently rotatable. The external shaft 16b can be rotated by a cable 30 and a pulley 32 coupled to the external shaft 16b. In addition, an upper pulley 34 is connected to the top of the external shaft 16b, with a cable 36 transmitting force/movement from the pulley 34 (associated with the external shaft) to a pulley 38 of the rotational linkage. Since a cable 36 is provided for transmitting movement to/from the pulley 38 to the external shaft 16b, all of the links of the FIG. 2C assembly are not necessary. In particular, the cable 36 eliminates the need for the links 14a and 14c (FIG. 2C). The pulley 38 corresponds to an elbow pivot (15c of FIG. 2C), while the arm 39 corresponds to a forearm member (e.g., as shown at 14d of FIG. 2C). The arm 40 pivots about a shoulder pivot 46 (corresponding, e.g., to the shoulder pivot 15a of FIG. 2C), such that rotation of the arm 40 about shoulder 46 positions the elbow 38, while rotation at the elbow 38 positions the forearm 39 (and thus the end effector) with respect to the elbow 38. The cable 30 can be connected to a pulley of an external drive source (not shown). Thus, a moving force can be imparted to the rotational system disposed inside of the MRI coil via the cable 30, with the moving force transmitted to the pulley/elbow portion 38 via the pulley 32, external shaft 16b, pulley 34, and cable 36. In addition, a moving force can be initiated by the patient moving the end effector 12 (not shown in FIG. 4), and the force or movement initiated by the patient is transmitted to the forearm 39, pulley 38, cable 36, pulley 34, shaft 16b, and pulley 32 so that measurements associated with a particular force/movement can be recorded or stored. In addition, a combination of the foregoing can be utilized, for example, if a task is to be performed by a patient which is opposed by a predetermined amount of force, or if the patient is to perform a task and it is desired to provide one or more interruptions or perturbations to that task by a force introduced while the patient is attempting to perform the task.

Still referring to FIG. 4, an additional cable 42 extends about a pulley 44, with the pulley 44 in turn connected to the internal shaft 16a, and with the internal shaft 16a connected to the shoulder 46 of the linkage. Thus, the cable and pulleys associated with the external shaft 16b provide for movement about the elbow, while the cable and pulley arrangement associated with the internal shaft 16a provides for movement about the shoulder of the linkage.

Optical encoders 50, 52 are respectively associated with the pulley 34 (associated with elbow movement) and the shoulder 46 for providing positional information associated with a particular task. Of course, the position sensors can also provide velocity and/or acceleration information by associating the position information with time information. In addition, optical torque sensors 54, 56 are respectively associated with the pulleys 32, 44 for providing force measurements. It is to be understood that the locations of the sensors are provided as an illustration, and the position and/or force sensors can be provided at locations other than those specifically shown. Preferably, a tensioning device, such as a turnbuckle T, is associated with each of the cables to maintain the cables in a taut condition, thereby avoiding inaccuracies or imprecision which may result from slack or play in the system. Thus, with the movement about the elbow 38 and about the shoulder 34, movement in two degrees of freedom can be accomplished by or imparted to the patient, while the sensors provide one or more measurements relating to position, force and velocity associated with the movement or a task.

FIG. 5 shows an alternate actuator arrangement for a rotational robotic arrangement in which cylinder actuators are utilized instead of cables. The arrangement of FIG. 5 includes a cylinder 60 which is coupled to the external shaft 16b via a suitable joint 62. The joint 62 may be of any form suitable for translating linear movement of the cylinder 60 into rotary movement, such that the external shaft 16b rotates in response to linear movement of the cylinder 60. By way of example, the joint 62 can be a pulley or disk, or a gear/pinion which meshes with a rack disposed on the cylinder 60. Rotation of the external shaft 16b rotates the disk 64, which in turn rotates a first arm 66 fixed to the disk 64. A second arm 68 is pivotally connected to the first arm 66. The arm 68 in turn is pivotally connected to a third arm or forearm part 70, while the arm 70 is connected to the elbow 72. As a result, rotation of the external shaft 16b results in movement of the arm 70 about the elbow. The end effector (not shown in FIG. 5) is coupled to the forearm part 70.

A fixed piston 74 is disposed inside of the cylinder 60, with the fixed piston 74 mounted upon a fixed rod 76.

The piston 74 divides the cylinder 60 into two chambers 78, 80, such that the cylinder 60 moves along the rod 76 by supplying hydraulic fluid to the chamber 78 or to the chamber 80, depending upon the direction of desired movement. A suitable supply/pump for hydraulic fluid is provided (not shown) to control the flow of fluid to and from the chambers 78, 80. A similar cylinder arrangement 82 is provided for moving the arm 71 about a shoulder 69 via the joint 84 and internal shaft 16a. As with the cylinder 60, the cylinder 82 includes a fixed piston 86 mounted upon a fixed rod 88, such that the cylinder 82 moves along the rod 88 depending upon whether hydraulic fluid is supplied to chamber 90 or chamber 92. As in the cable actuator arrangement, optical encoders can be provided as shown at 50, 52. Torque sensors can be provided at the same locations depicted in FIG. 4 for force measurements. Alternatively, the optical position and/or torque sensors can be provided in the region adjacent the cylinders 60, 82. As a further alternative, it is also possible to correlate force movements with the pressure of hydraulic fluid supplied to the cylinders 60, 82, and/or to provide position sensing by optically detecting indicia or notches disposed upon the cylinders 60, 82, such that the linear movement of the cylinders is detected rather than the rotary movement detected by the optical encoders 50, 52. Other sensing arrangements are also possible. For example, an optical position or motion detector could be disposed outside of the MRI, with light directed into the MRI to determine the position of one or more components of the robotic system. It is to be understood that a hybrid of the cable and cylinder actuator arrangements is also possible, as are other types of actuators. Although alternate linkage arrangements are possible, the FIG. 5 arrangement can utilize a five bar linkage as shown in FIG. 2C, with the arm 66 corresponding to arm 14a, arm 71 corresponding to arm 14b, arm 68 corresponding to arm 14c, arm 70 corresponding to arm 14d, shoulder 69 corresponding to shoulder pivot 15a, and elbow pivot 72 corresponding to elbow pivot 15c.

Figure 6:
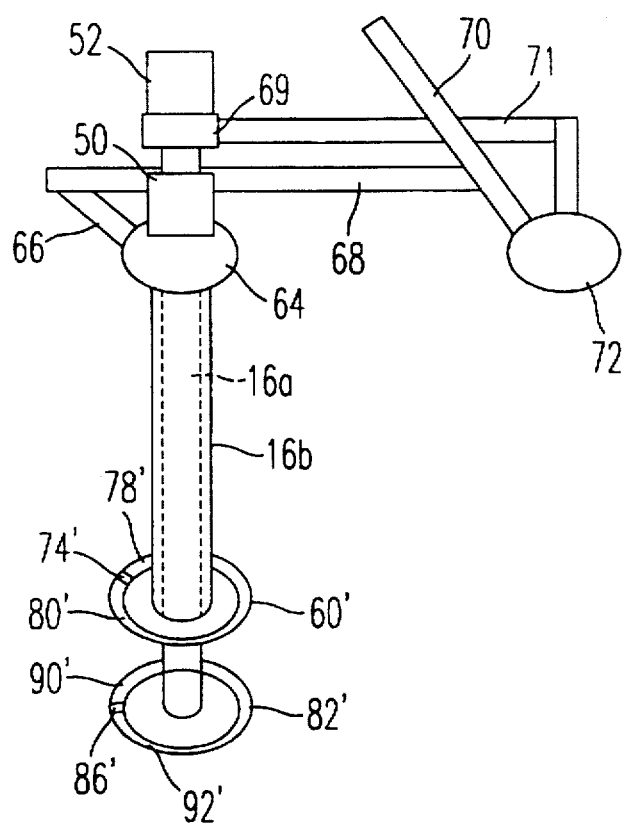
FIG. 6 is a modified form of the arrangement of FIG. 5. in which annular hydraulic actuators are utilized.

FIG. 6 provides a further alternate actuator arrangement in which annular cylinders 60', 82' are utilized in place of the linear cylinders 60, 82 of FIG. 5. With this arrangement, rather than extending linearly, the cylinders are shaped as an annulus, having a fixed piston 74', 86' disposed therein, such that the fixed piston divides the cylinders into chambers 78', 80 ', 90 ', 92'. Thus, depending upon the chamber to which fluid is supplied (or in other words, which side of the piston is supplied with fluid), the cylinders 60', 82' rotate, to thereby rotate the internal and external shafts, and control movement of or impart forces to the five-bar linkage.

Figure 7A:
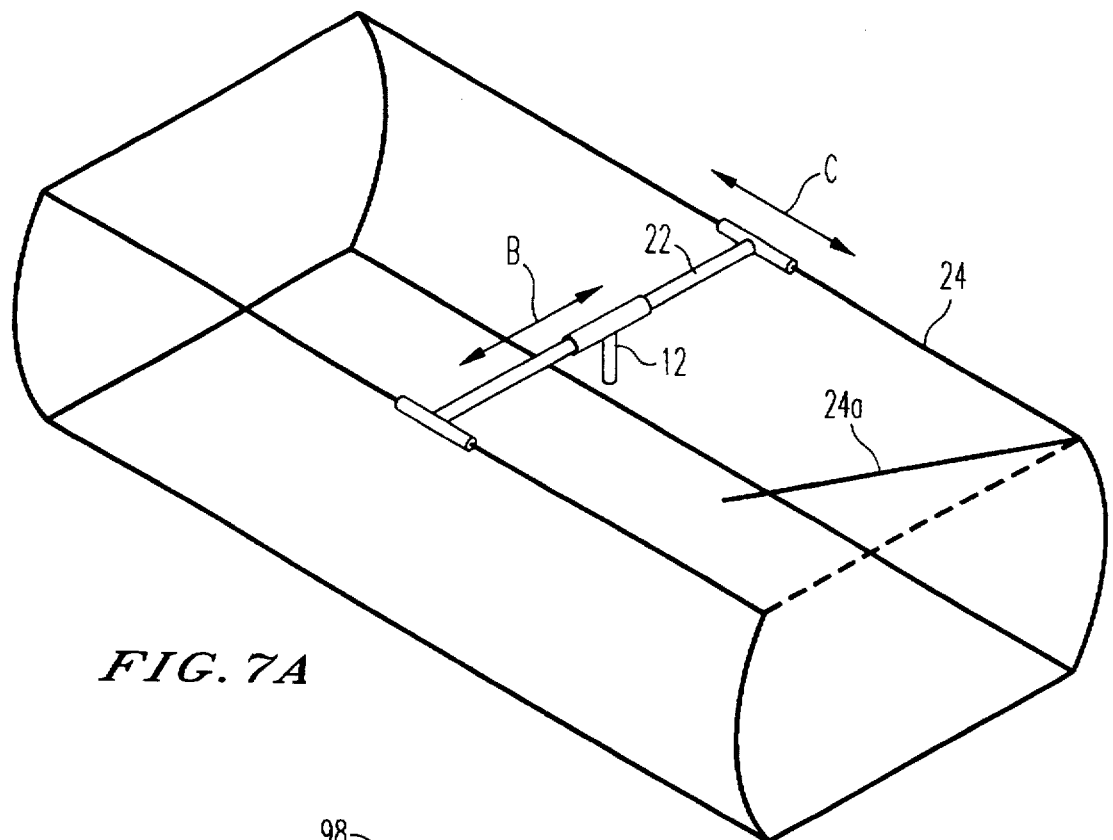
FIG. 7A is a perspective view of a frame for the Cartesian embodiment of the present invention.
Figure 7B:
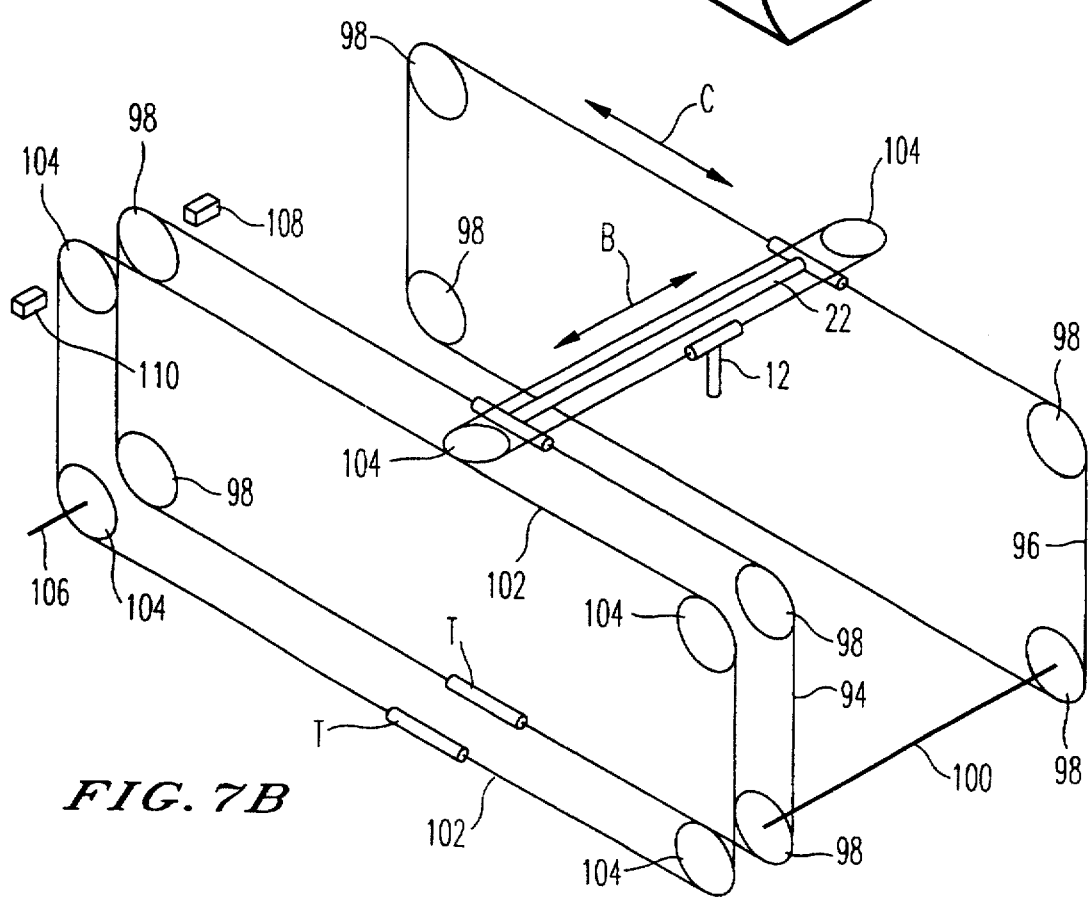
FIGS. 7B–7E depict different actuator and sensor arrangements which can be utilized with the Cartesian robot embodiment of the present invention.

FIG. 7A is a perspective view a frame 24 for the Cartesian embodiment of the robot, while FIG. 7B depicts a cable driven actuator arrangement which can be utilized in the Cartesian configuration. As shown in FIGS. 7A and 7B, the end effector 12 is movable in the transverse direction B along transverse arm 22, while the transverse arm 22 is movable in the longitudinal direction C along the frame 24. If desired, one or more components of the frame 24 can be movable to ease access to the interior of the frame. For example, a bar 24a can be pivotally mounted so that it can be moved to an open position (as shown in FIG. 7A) when a patient is entering the frame. The frame 24 provides a mounting assembly for the end effector 12, and for the actuator system (e.g., pulleys and cables or hydraulic cylinders) as will now be discussed.

As shown in FIG. 7B, a pair of cables 94, 96 can be provided for the longitudinal (arrow C) movement of the transverse arm 22, with the cables 94, 96 disposed about a plurality of pulleys 98. Two of the pulleys 98 are fixed to a drive shaft 100, and the drive shaft 100 is connected to an external drive system (not shown). The shaft 100 drives the cables 94, 96, thus longitudinally moving (arrow C) the transverse arm 22, which is coupled to the cables 94, 96. Although it is possible to provide the longitudinal movement utilizing a single cable rather than a pair of cables 94, 96, a pair of cables 94, 96 are provided for a more-balanced movement in the longitudinal direction. Turnbuckles T can be provided to stretch or ensure tautness of the cables, thus preventing any play and imprecision/inaccuracy associated therewith. An additional cable 102 is disposed about a plurality of pulleys 104 for driving the handle 12 in the transverse direction (i.e., along the transverse arm 22). One of the pulleys 104 is driven by a transverse drive shaft 106, with the drive shaft 106 connected to a transverse drive system (not shown). Optical encoders 108, 110 can be associated with each of the cable systems, such that the combined sensing of the cables (e.g., 94 and 102), determines the position and movement of the end effector 12. The encoders can sense movement of the pulleys 98, 104, or can sense indicia provided on the cables 94, 102. Alternately, it is also possible to sense position by recording rotational movement of the draft shafts 100, 106. Torque sensors can also be associated with the drive shafts 100, 106.

In the arrangement of FIG. 7B, since the cable 102 extends in longitudinal and transverse directions as shown, movement of the arm 22 in the longitudinal direction will result in transverse movement of the end effector 12 if the drive 106 for the transverse movement is not moved, since the pulley 104 at the left side of the arm 22 will walk along the cable 96 as the arm 22 is moved in the longitudinal direction. Thus, movement in the longitudinal direction must be compensated with a corresponding drive of the transverse drive shaft 106. By way of example, if the handle 12 is desired to be maintained in a fixed transverse position while the arm 22 is moved longitudinally, the drive shaft 106 must be rotated during the longitudinal movement to maintain the end effector 12 in the desired transverse position.

Figure 7C:
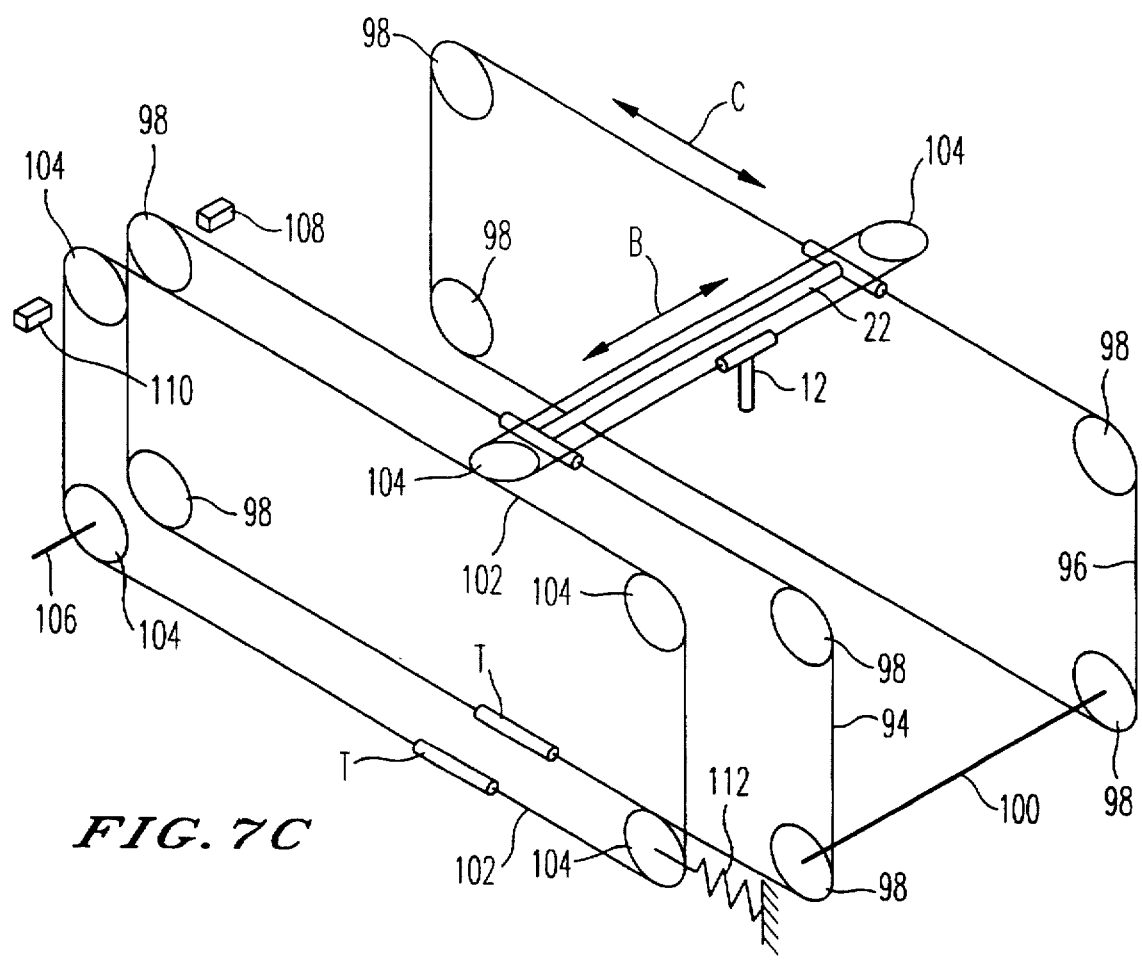

The arrangement of FIG. 7C provides a self-adjusting or self-compensating arrangement, such that the transverse drive shaft 106 need only be driven when movement in the transverse direction is desired. In this arrangement a differential mechanism, schematically represented at 112, is provided between pulleys 98 of the longitudinal drive system and pulleys 104 of the transverse drive system, such that a compensating drive of the drive shaft 106 is not needed to compensate for longitudinal movement of the transverse arm 22.

Figure 7D:
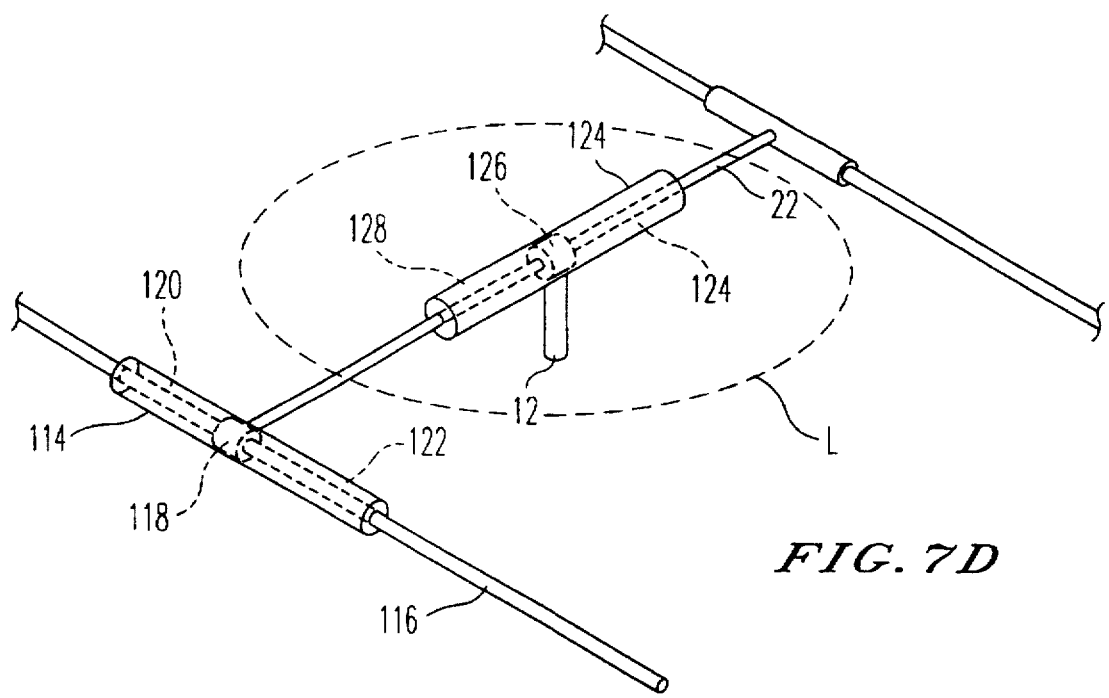

FIG. 7D depicts an alternate actuator assembly for the Cartesian configuration in which a cylinder 114 is movably mounted upon a fixed rod 116. A piston 118 is fixed to the rod 116, such that the cylinder 114 is moved by supplying a fluid to the chamber 120 or the chamber 122 depending upon the desired direction of movement. The transverse arm 22 is connected to the cylinder 114, such that movement of the cylinder 114 results in longitudinal movement of the arm 22. For illustrative purposes, the transverse arm assembly 22 (disposed in the region designated by the broken line L in FIG. 7D) is shown separately in FIG. 7D. The end effector 12 is mounted to a cylinder 124, with a piston 126 fixed to the transverse arm 22 such that the cylinder 124 is moved along arm 22 by supplying hydraulic fluid to either the chamber 128 or the chamber 130. Thus, longitudinal movement is provided by the cylinder 114, while the transverse movement is provided by the cylinder 124. The hydraulic fluid for the chambers of the cylinders 114, 124 can be supplied by tubing which extends through or along the frame (24) of the Cartesian configuration.

Figure 7E:
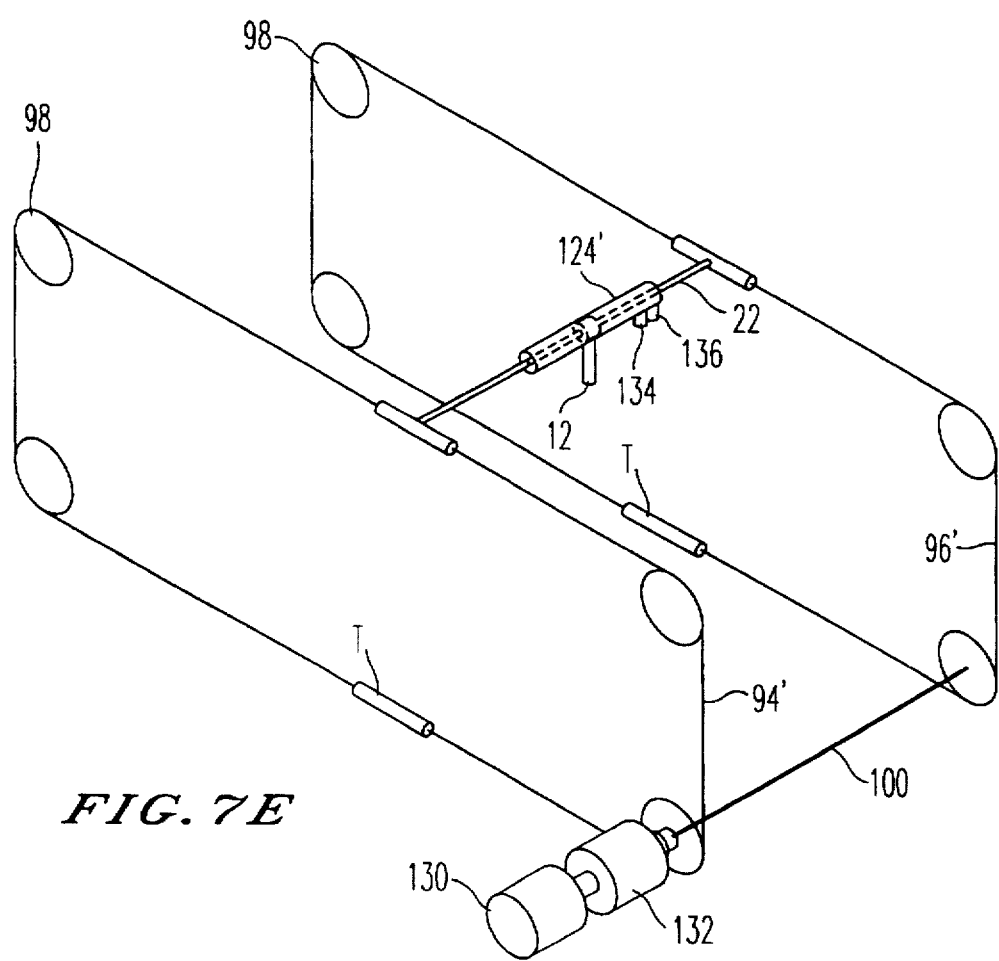

It should be recognized that combinations of the foregoing actuator arrangements are also possible, as are alternate actuators. By way of example, FIG. 7E shows a hybrid of the cable and cylinder embodiments, in which cables 94', 96' are provided for longitudinal movement, while a cylinder arrangement 124' is provided for the transverse movement. Optical and force/torque sensors 130, 132 can be associated with the longitudinal drive system, or a drive shaft 100 of the longitudinal drive system, while position and force sensors 134, 136 are also provided for the transverse movement. The position sensing for the transverse movement can be provided by an optical encoder disposed on the frame 24 or on the transverse arm 22, with the encoder detecting movement of the cylinder 124' with respect to the arm 22. Alternately, the encoder can be mounted upon the cylinder 124' for sensing movement of the cylinder 124 ' with respect to the arm 22, e.g., by sensing indicia or notches disposed on the arm 22. The force sensor for the transverse movement can sense hydraulic pressure supplied to the cylinder 124', or can include a strain gauge or deformation-based sensor disposed on the arm 22 or the end effector 12.

Figure 8B:
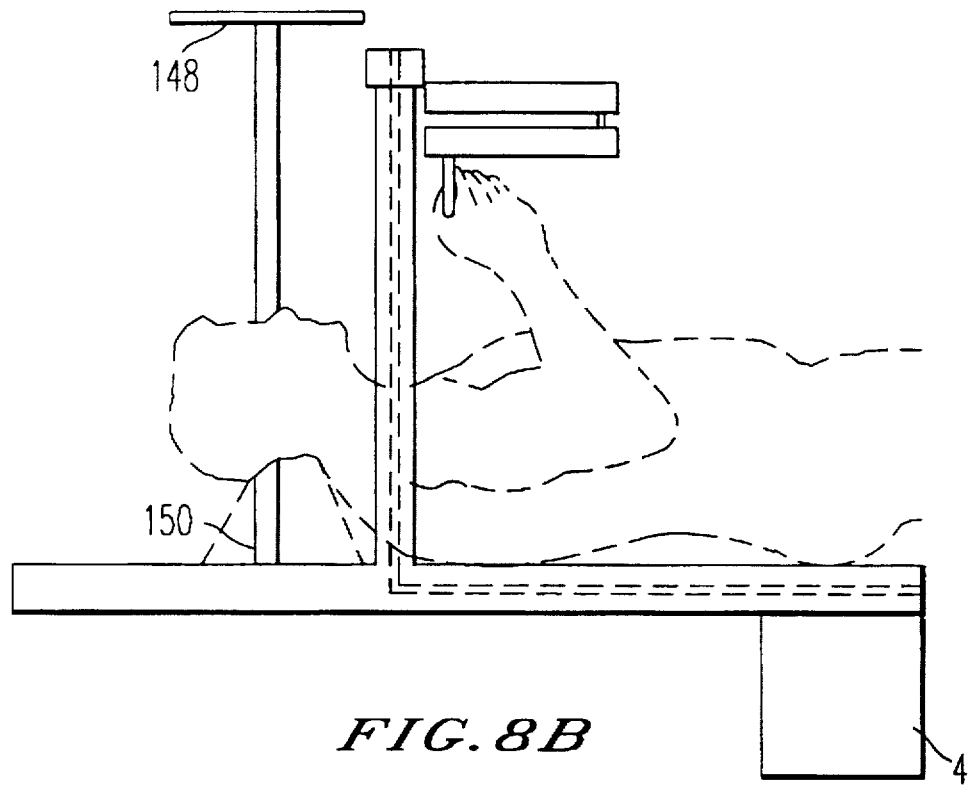
Figure 8C:
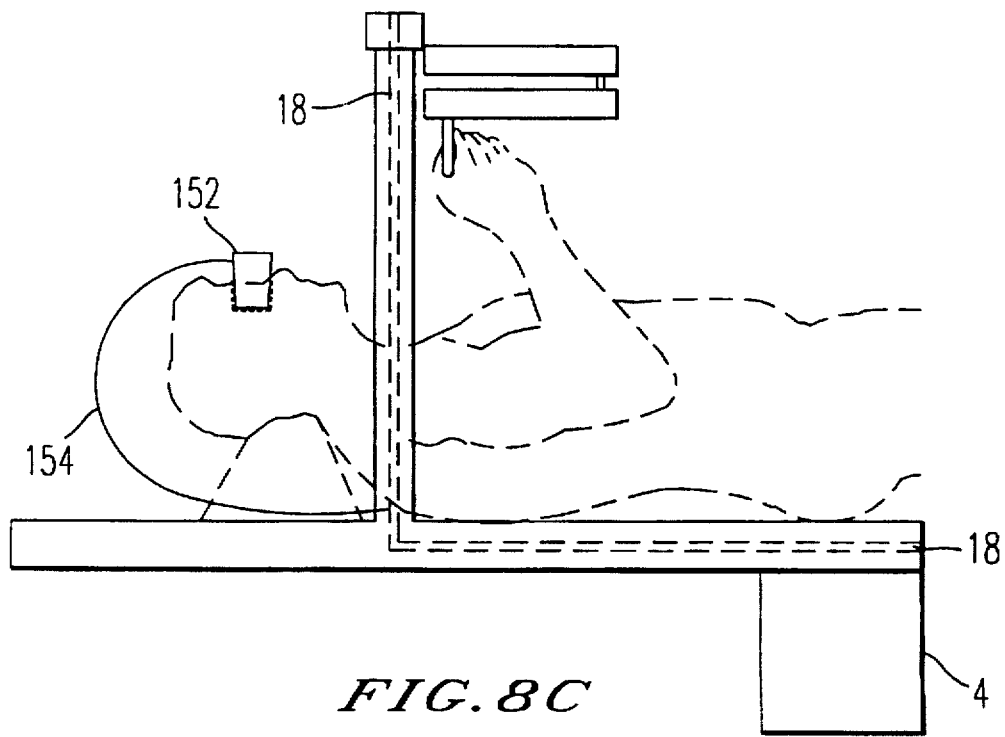

FIGS. 8A–8C depict various arrangements to provide the subject or patient with visual information. In the context of a handle member being provided as an end effector, the visual information can be utilized to instruct a patient while the patient is learning a particular manipulative task, and can also instruct the patient to perform a previously learned task. The visual information can also be utilized for instructional information where the end effector engages various other body segments, for example to inform the patient to move a body segment, cough, breathe deeply, etc. In the arrangement of FIG. 8A, a projector 140 projects an image or instructions onto a screen 142, which the patient views via a mirror 144 disposed inside of the MRI coil 2. Since the patient views the image via mirror 144, the instructions or image projected onto the screen 142 should be an inverse or mirror image of the image desired to be viewed by the patient.

In the arrangement of FIG. 8B, a display screen 148 is disposed inside of the MRI coil. The display screen can be supported by a column 150, or if the Cartesian configuration is utilized, the display screen can be supported by the frame 24. Information is provided fiber optically (by optical fibers which can extend through the post 150 or the Cartesian frame 24), and the information is projected onto the screen 148 to magnify the image/information delivered fiber-optically. Alternately, as shown in FIG. 8C, goggles 152 having a visual display associated therewith can be provided for supplying visual information to the patient via fiber optics 154. If desired, the same passageway can be utilized for fiber optic visual information and for the fiber optics/light utilized for sensing/measuring movement and forces of the robotic system, as shown at 18.

Figures 9A, 9B:
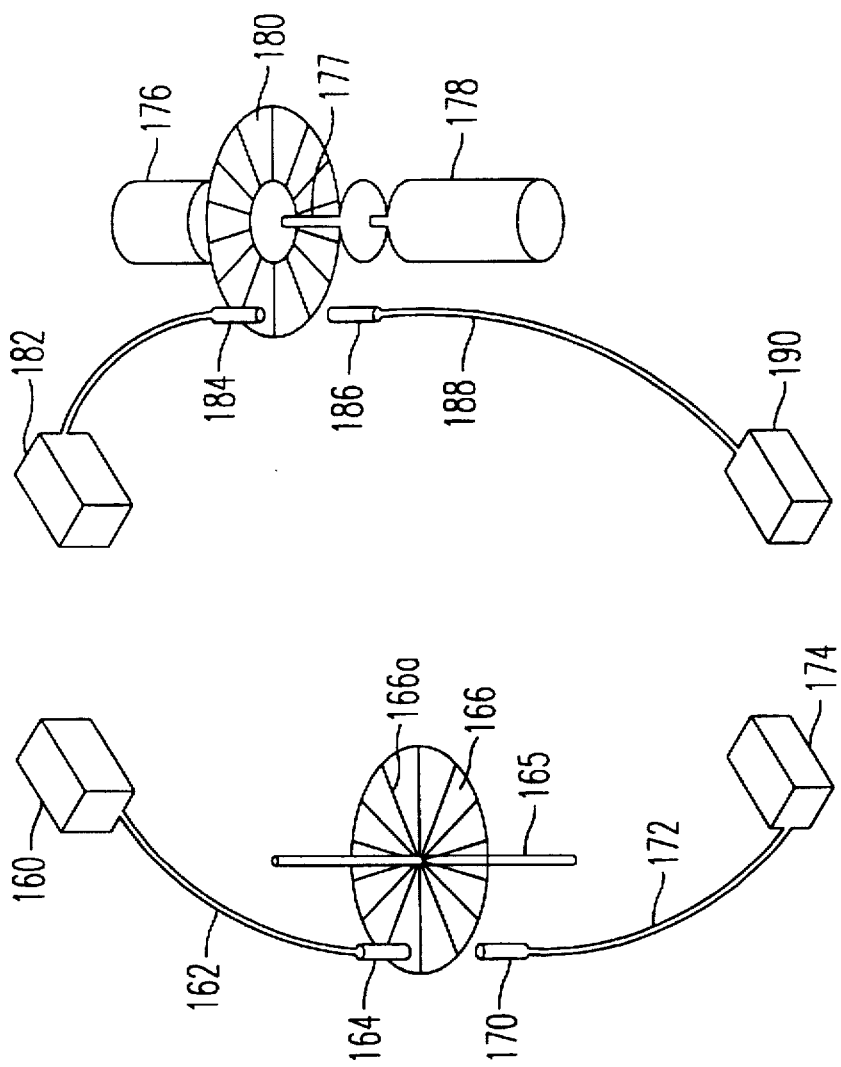
FIGS. 9A and 9B. respectively. depict position and torque/force sensors for use in the robotic systems of the present invention.

FIGS. 9A and 9B, respectively, are examples of position and torque/force sensor arrangements which can be utilized for providing sensed/measured information associated with operation of the robotic system. As shown in FIG. 9A, a remote light source 160 can be provided outside of the MRI coil, with the light source delivering light via fiber optics 162 to a light input location 164 adjacent a rotary optical encoder disk 166. The disk 166 includes a plurality of slots 166a or other indicia thereon, such that rotation of the disk 166 (e.g., about shaft 165 or the disk can be supported on a shoulder or elbow of the robot for rotation therewith) provides a pulsed light on the opposite side of the disk 166, which is read by a light reader 170. The signal from the light reader 170 is then conveyed outside of the MRI coil, via fiber optics 172, to a transducer 174 which is located outside of the MRI coil. The disk 166 can be coupled to a pulley, cable, hydraulic cylinder, or an arm or pivot location (i.e., in a rotational linkage arrangement) to provide positional information regarding movement of the robot.

The torque sensor shown in FIG. 9B is deformable in response to a force or torque, such that a first part 176 deforms or rotates with respect to a second part 178 when a torque is applied, with the amount of rotation of the first part 176 with respect to the second part 178 corresponding to the amount of torque applied across the torque sensor. The amount of torque (imparted, e.g., to a drive shaft, a pulley, robotic arm etc.) is thus measured by the amount of rotation of an encoder disk 180. The disk 180 is fixed to either the first part 176 or second part 178, while the light introducing element 184 is connected to or fixed with respect to the other of the first and second parts 176, 180. Deformation in the torque sensor can be provided by utilizing a deformable member in the form of a shaft 177 which deforms in response to a torque, or the deformable member can be by a spring or deformable member disposed inside of the cylinder body of either the first part 176 or the second part 178. As with the position sensing, an external light source 182 supplies light to a location 184 adjacent to the encoder disk 180, with the force information read by the light reader 186 and conveyed fiber optically (188) to an external transducer 190.

Figure 10:
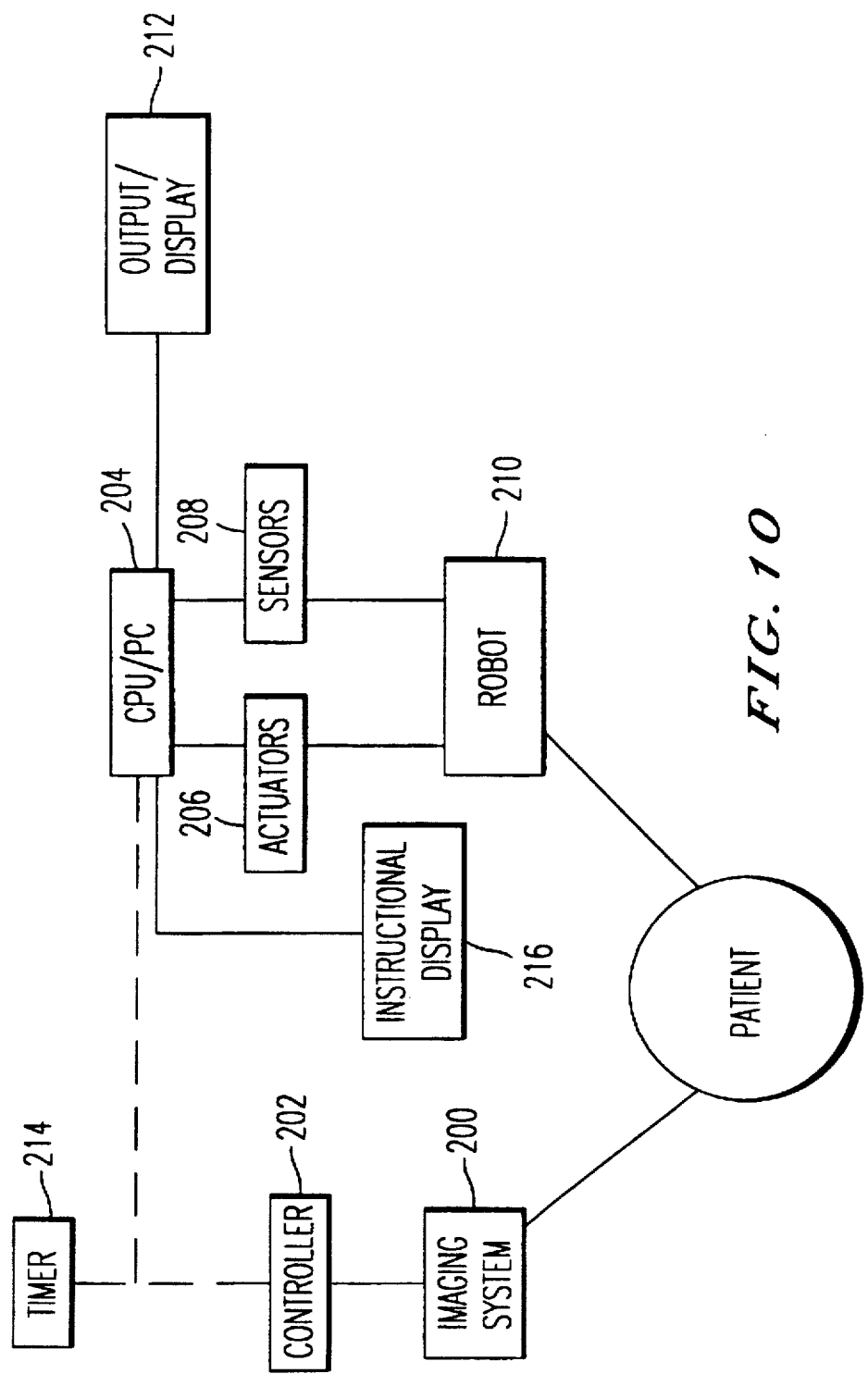
FIG. 10 schematically represents the overall robotic imaging system of the present invention.

FIG. 10 schematically represents the overall arrangement for practicing the method and apparatus of the present invention. The arrangement includes an imaging system and associated controller 200, 202, which in and of themselves are known. The controller 202 controls the taking of images utilizing the imaging system 200. As discussed earlier, preferably images are taken at a relative rapid rate, e.g., on the order of one image every hundred or hundreds of milliseconds, up to one image per second. A central processing unit or personal computer is provided as shown at 204 for controlling operation of the robot 210 via actuators 206. The computer 204 also records the sensed or measured position and force information as provided by the sensors 208. In addition, the sensors provide feedback for controlling the actuators, for example, to indicate when a desired position has been reaches so that operation of the actuators is halted. The computer 204 thus receives and stores information from the transducers (e.g. 174, 190 of FIGS. 9A and 9B) associated with the sensors, and also provides controlling instructions for the actuators. The control signals for the actuators are sent to servo actuators (a servoamplifier and motor) for driving cables associated with a cable actuator arrangement, or to a hydraulic pump or pumps for the hydraulic cylinder actuator arrangements.

If desired, the computer/controller for controlling the robot can be coupled to the controller 202 for the imaging system, such that the computer 204 instructs the controller 202, e.g., as to the timing of image taking, or so that a common output display 212 includes both image information and information regarding robotic movement (position, velocity force, etc.). However, the computer/controller 204 for the robotic system need not be coupled to the controller 202 for the imaging system, and therefore, they are shown as optionally connected in a broken line in FIG. 10. The images may also be correlated by an attendant (e.g., a technician or doctor) by associating the robotic system information for a particular task with the image information obtained during the task. Further, it may be optionally desired to provide a common timer 214, so that the image taking and robot control (and/or measurements associated with the robot) can be coordinated (or synchronized) and correlated with one another on the basis of time. An additional display 216 can also be controlled by the computer 204, to provide instructions to the patient (in the form of visual images or verbal/written instructions).

The software for controlling operation of the actuators can include plural preprogrammed sequences, and can also allow a new sequence to be manually input, or a preprogrammed sequence to be modified. The preprogrammed sequences control the actuator system. For example, if the robotic system is provided in the form of a handle member as the end effector, the preprogrammed sequences can guide the patient through various tasks, and/or can control the actuators to resist or provide an unexpected perturbation while the patient is attempting to perform a task. Of course, alternate preprogrammed sequences are also possible, for example, if the end effector is utilized to apply a pressure or force (static, increasing/decreasing, intermittent, etc.), to the body segment engaged by the end effector during imaging.

If an instructional display 216 is utilized, various preprogrammed actuator sequences can be associated with one or more displays. For example, in the manipulative task context, preprogrammed sequences can be provided so that the patient encounters a perturbation when attempting to perform a task instructed by the display 216. In addition, the robot may be utilized to input a particular sequence, such that, e.g., a therapist can utilize the robot to input a task which is stored by the computer 204, and with the computer 204 thereafter displaying the sequence visually at 216, or using the sequence to control the actuators 206 to guide a patient through a sequence which has been input utilizing the robot. The preprogrammed sequences can also instruct the actuators to perform a palpation or engage a particular body segment during an instructed task, e.g., when the patient instructed to cough or breathe deeply. Additional examples for controlling the robot and/or for displayed information for use with the robot are disclosed in allowed U.S. application Ser. No. 08/178,182, which is incorporated herein by reference.

As should be apparent from the foregoing, in accordance with the present invention, a robotic device is provided which can be utilized within an imaging system, such that the robotic device controls and/or provides measured information as to the mechanical environment within the imaging system while images are obtained. The invention can be utilized for various diagnostic and therapeutic purposes, as well as in advancing understanding of various biological systems. For example, the present invention can be utilized to measure motor performance while imaging the brain to determine brain activity (e.g., by measuring the blood oxygenation). Further, by way of example, where the end effector is implemented as a handle member while obtaining images, the robotic system can measure performance associated with a variety of tasks and conditions including: (1) while the patient is practicing a visually displayed or visually instructed task, (2) while the patient is in an early motor learning stage (while the patient is learning a task), and with the robot optionally perturbing the performance of the patient, and/or (3) in late motor learning when the patient is performing a task which has been practiced sufficiently such that the patient is comfortable with the task, and with the performance of the task optionally perturbed by the robot. Further, if desired, rather than utilizing a visual display, the patient can be guided through a sequence utilizing the actuators of the robotic system, and the patient's resistance to such guidance can also be measured by the robotic system. Moreover, the end effector can be implemented in a variety of forms other than a handle member, with the end effector engaging a body segment while the robotic system controls and measures the mechanical environment during imaging.

obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters: Patent of the United States is:

1. A robotic system for use in an imaging system comprising:
   an end effector adapted to engage a body segment of a patient;
   a mounting assembly movably mounting said end effector wherein said end effector and said mounting assembly are formed of magneto-translucent materials;
   a position sensing system for providing positional information of the end effector;
   an actuator system for moving said end effector; and
   wherein said position sensing system includes a magneto-translucent encoder coupled to one of said mounting assembly and said end effector of said robotic system.

2. A robotic system as recited in claim 1, wherein said actuator system includes at least one actuator formed of magneto-translucent materials.

3. A robotic system as recited in claim 2, wherein said at least one actuator comprises a cable system.

4. A robotic system as recited in claim 2, wherein said at least one actuator comprises a hydraulic cylinder.

5. A robotic system as recited in claim 1, wherein said position sensing system further includes a light source, a first optical cable extending from said light source to a first location adjacent said magneto-translucent encoder, a transducer, and a second optical cable extending from a second location adjacent said magneto-translucent encoder to said transducer.

6. A robotic system as recited in claim 1, further including a force sensing system for sensing forces applied to said end effector.

7. A robotic system as recited in claim 6, wherein said force sensing system includes a magneto-translucent deformable member coupled to one of said end effector and said mounting assembly.

8. A robotic system as recited in claim 7, further including means for storing information sensed by said position sensing system and said force sensing system.

9. A robotic system as recited in claim 8, wherein said means for storing comprises a computer, and wherein said computer includes means for controlling said actuator system.

10. A robotic system as recited in claim 6, further including means for storing information sensed by said position sensing system and said force sensing system.

11. A robotic system as recited in claim 10, wherein said means for storing comprises a computer, and wherein said computer includes means for controlling said actuator system.

12. A robotic system as recited in claim 1, further including means for storing information sensed by said position sensing system.

13. A robotic system for use in an imaging system comprising:
    an end effector adapted to engage a body segment of a patient;
    a mounting assembly movably mounting said end effector;
    a position sensing system for providing positional information of the end effector; and
    an actuator system for moving said end effector;
    the robotic system further including a force sensing system for providing force information of forces applied to said end effector, wherein said force sensing system includes a magneto-translucent deformable member coupled to one of said end effector and said mounting assembly.

14. A robotic system as recited in claim 13, wherein said force sensing system further comprises a light source, a transducer, an optical cable extending from said light source to a first location adjacent said deformable member, and a further optical cable extending from a second location adjacent said deformable member to said transducer.

15. A diagnostic/therapeutic imaging system comprising:
    (a) an imaging system for obtaining an image of a first body segment of a patient;
    (b) a robotic system including:
       (i) an end effector adapted to engage a second body segment of a patient while said imaging system is obtaining an image of said first body segment, and wherein said end effector is selectively movable in a plurality of degrees of freedom; and
       (ii) a sensing system for sensing movement of said end effector and providing sensed information for correlation with an image of said first body segment obtained by said imaging system;
    wherein said robotic system is at least partially disposed within said imaging system.

16. A diagnostic/therapeutic imaging system as recited in claim 15, further including an actuator system for moving said end effector.

17. A diagnostic/therapeutic imaging system as recited in claim 15, further including a computer for storing information sensed by said sensing system, and wherein said computer controls said actuator system.

18. A diagnostic/therapeutic imaging system as recited in claim 17, wherein said computer stores a plurality of pre-programmed sequences for controlling said actuator system.

19. A diagnostic/therapeutic imaging system as recited in claim 15, further including an instructional display for instructing a patient to perform a task.

20. A diagnostic/therapeutic imaging system comprising:
    (a) an imaging system for obtaining an image of a first body segment of a patient;
    (b) a robotic system including:
       (i) an end effector adapted to engage a second body segment of a patient while said imaging system is obtaining an image of said first body segment, and wherein said end effector is selectively movable in a plurality of degrees of freedom; and (ii) a sensing system for sensing movement of said end effector and providing sensed information for correlation with an image of said first body segment obtained by said imaging system;

wherein said imaging system comprises a magnetic resonance imaging system, and wherein said end effector and at least part of said sensing system are formed of magneto-translucent materials, the diagnostic/therapeutic imaging system further including means for recording movement of said end effector, wherein said means for recording movement is disposed outside of said imaging system.

21. A diagnostic/therapeutic imaging system comprising:

(a) an imaging system for obtaining an image of a first body segment of a patient;

(b) a robotic system including:
  (i) an end effector adapted to engage a second body segment of a patient while said imaging system is obtaining an image of said first body segment, and wherein said end effector is selectively movable in a plurality of degrees of freedom; and
  (ii) a sensing system for sensing movement of said end effector and providing sensed information for correlation with an image of said first body segment obtained by said imaging system;

(c) wherein said sensing system includes:
  an encoder for sensing movement of said end effector, said encoder including an encoder disk disposed in said imaging system;
  (ii) a light source disposed outside of said imaging system; and
  (iii) an optical cable extending from said encoder disk to said light source.

22. A diagnostic/therapeutic imaging system as recited in claim 21, wherein said sensing system further includes a transducer disposed outside of said imaging system, and an additional optical cable extending from said encoder disk to said transducer, and wherein said transducer is connected to means for recording movement.

23. A diagnostic/therapeutic imaging system comprising:

(a) an imaging system for obtaining an image of a first body segment of a patient;

(b) a robotic system including:
  (i) an end effector adapted to engage a second body segment of a patient while said imaging system is obtaining an image of said first body segment, and wherein said end effector is selectively movable in a plurality of degrees of freedom; and
  (ii) a sensing system for sensing movement of said end effector and providing sensed information for correlation with an image of said first body segment obtained by said imaging system;

(c) wherein the system further includes an optical strain gauge comprising:
  (i) a deformable member coupled to said robotic system such that said deformable member is deformed in response to a force applied to said end effector;
  (ii) a light source disposed outside of said imaging system; and
  (iii) an optical cable extending from said deformable member to said light source.

24. A diagnostic/therapeutic imaging system as recited in claim 23, further including an encoder disk coupled to said deformable member.

25. A diagnostic/therapeutic imaging system as recited in claim 24, further including a transducer disposed outside of said imaging system and an additional optical cable extending from said deformable member to said transducer.

26. A diagnostic/therapeutic imaging system comprising:

(a) an imaging system for obtaining an image of a first body segment of a patient;

(b) a robotic system including:
  (i) an end effector adapted to engage a second body segment of a patient while said imaging system is obtaining an image of said first body segment, and wherein said end effector is selectively movable in a plurality of degrees of freedom; and
  (ii) a sensing system for sensing movement of said end effector and providing sensed information for correlation with an image of said first body segment obtained by said imaging system;

(c) an instructional display for instructing a patient to perform a task; and (d) wherein the system further includes a computer which stores information sensed by said sensing system, and wherein said computer stores a plurality of images to be displayed by said instructional display.

27. A diagnostic/therapeutic imaging system as recited in claim 26, further including an actuator system for applying forces to the robotic system, and wherein said computer controls said actuator system.

28. A diagnostic/therapeutic imaging system as recited in claim 27, wherein said computer stores a plurality of actuator sequences.

29. A diagnostic/therapeutic imaging system as recited in claim 28, wherein said plurality of actuator sequences includes at least one perturbing sequence to provide a force opposing a patient while a patient is performing a task instructed by said instructional display.

30. A robotic system for use in a diagnostic/therapeutic imaging, comprising:

(a) an end effector to be disposed within an imaging system, said end effector providing a coupling between the robotic system and a body segment of a patient, said end effector formed of a magneto-translucent material;

(b) a mounting assembly for movably mounting said end effector;

(c) at least one sensor component coupled to one of said mounting assembly and said end effector, said at least one sensor component including at least one of:
  (i) an encoder disk which moves in response to movement of said end effector; and
  (ii) a deformable member which deforms in response to a force applied to said end effector;

(d) a light source; and (e) an optical cable extending from said light source to said at least one sensor component.

31. A robotic system as recited in claim 30, further including an actuator system coupled to said mounting assembly for imparting a force to said end effector.

32. A robotic system as recited in claim 31, further including control means for recording information sensed by said at least one sensor component, and wherein said control means controls said actuator system.

33. A robotic system as recited in claim 32, further including instructional display means for providing a patient with instructions to perform a task while said end effector engages a body segment, and wherein said control means controls said actuator system to provide a perturbing force while a patient is attempting to perform a task instructed by said instructional display means.

21

34. A robotic system as recited in claim 30, wherein a plurality of sensor components are provided for sensing position and force information associated with movement of said handle member, the robotic system further including an actuator system for moving said end effector and for providing an opposition force opposing movement of the end effector by a patient.

35. A robotic system as recited in claim 30, wherein said mounting assembly movably mounts said end effector for selectable and variable movement in at least two degrees of freedom.

36. An imaging method utilizing a robotic system, comprising:

providing a robotic system having an end effector selectively movable in at least two degrees of freedom to allow performance of a plurality of different tasks;

coupling the end effector to a body segment of a patient;

sensing at least one of: (a) a force applied to said end effector, and (b) a position of said end effector;

obtaining at least one brain image during the sensing step; and correlating the at least one brain image to information obtained during said sensing step.

37. A method as recited in claim 36, further including providing said robotic system with a plurality of actuators for imparting a force to said end effector.

38. A method as recited in claim 36, wherein said sensing step includes taking position and force measurements.

39. A method as recited in claim 36, wherein said end effector is a handle member adapted to engage an extremity of a patient, the method further including sensing position of said end effector and sensing forces applied to said end effector while said patient is performing a task with said handle member.

40. An imaging method as recited in claim 36, further including providing an actuator system for moving said end effector, and wherein the step of obtaining at least one brain image includes obtaining at least one brain image while said end effector is being moved by said actuator system.

41. An imaging method utilizing a robotic system, comprising:

providing a robotic system having an end effector selectively movable in at least two degrees of freedom to allow performance of a plurality of different tasks;

coupling the end effector to a body segment of a patient;

sensing at least one of: (a) a force applied to said end effector, and (b) a position of said end effector;

obtaining at least one image during the sensing step;

wherein said end effector is a handle member adapted to engage an extremity of a patient, the method further including sensing position of said end effector and sensing forces applied to said end effector while said patient is performing a task with said handle member;

wherein the step of obtaining an image includes obtaining an image utilizing a magnetic resonance imaging system, and wherein at least a portion of said robotic system is disposed inside of said magnetic resonance imaging system; and

22 wherein the sensing step includes providing a plurality of sensor components inside of said magnetic resonance imaging system, providing at least one light source outside of said magnetic resonance imaging system, and providing optical cables for feeding light from said at least one light source to said plurality of sensor components.

42. A method as recited in claim 41, wherein the step of obtaining at least one image includes obtaining a brain image.

43. A diagnostic/therapeutic imaging system comprising:

(a) a magnetic resonance imaging system; and (b) a robotic system including:

(i) an end effector adapted to engage an extremity of a patient during imaging of said patient by said magnetic resonance imaging system;

(ii) a mounting assembly for movably mounting said end effector such that said end effector is selectively movable in a plurality of degrees of freedom;

(iii) an actuator system for moving said end effector and thereby moving the extremity of the patient;

(iv) position sensor means for sensing position of said end effector; and (v) control means for controlling said actuator system to cause said actuator system to move said end effector.

44. A diagnostic/therapeutic imaging system as recited in claim 43, further including force sensing means for sensing forces associated with movement of said end effector.

45. A diagnostic/therapeutic imaging system as recited in claim 44, wherein said control means stores a plurality of actuator system sequences.

46. A diagnostic/therapeutic imaging system as recited in claim 45, wherein said control means stores information obtained by said position sensor means and said force sensor means.

47. A diagnostic/therapeutic imaging system as recited in claim 43, wherein at least part of said robotic system is disposed inside of said magnetic resonance imaging system.

48. A robotic system for use in a magnetic field comprising:

(a) an end effector formed of a magneto-translucent material;

(b) a mounting assembly for movably mounting the end effector;

(c) a position sensor formed of a magneto-translucent material, said position sensor coupled to one of said end effector and said mounting assembly;

(d) a light source; and (e) an optical cable extending from said light source to said position sensor.

49. A robotic system as recited in claim 48, further including at least one actuator formed of a magneto-translucent material, and a force sensor formed of a magneto-translucent material.

* * * * *